US006942963B1

(12) United States Patent
Ingram et al.

(10) Patent No.: US 6,942,963 B1
(45) Date of Patent: Sep. 13, 2005

(54) METHODS FOR IDENTIFYING TREATMENTS FOR NEUROTOXICITY IN ALZHEIMER'S DISEASE CAUSED BY β-AMYLOID PEPTIDES

(75) Inventors: Vernon M. Ingram, Cambridge, MA (US); Barbara J. Blanchard, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 66 days.

(21) Appl. No.: 09/706,574

(22) Filed: Nov. 3, 2000

Related U.S. Application Data

(63) Continuation-in-part of application No. 09/005,215, filed on Jan. 9, 1998, now Pat. No. 6,172,043, which is a continuation of application No. 08/960,188, filed on Oct. 29, 1997, now abandoned.
(60) Provisional application No. 60/035,847, filed on Jan. 10, 1997.

(51) Int. Cl.$^7$ .............................................. C12Q 3/00
(52) U.S. Cl. ..................... 435/3; 435/808; 436/63; 436/164; 436/172; 436/182; 436/800; 436/805
(58) Field of Search ........................... 435/3, DIG. 14, 435/DIG. 15, 808; 436/63, 164, 172, 182, 800, 805

(56) References Cited

U.S. PATENT DOCUMENTS

| | | |
|---|---|---|
| 4,801,575 A | 1/1989 | Pardridge |
| 4,902,505 A | 2/1990 | Pardridge et al. |
| 4,918,162 A | 4/1990 | Slamon et al. |
| 4,933,324 A | 6/1990 | Shashoua |
| 4,975,430 A | 12/1990 | Jahr et al. |
| 5,004,697 A | 4/1991 | Pardridge |
| 5,108,921 A | 4/1992 | Low et al. |
| 5,112,596 A | 5/1992 | Malfroy-Camine |
| 5,268,164 A | 12/1993 | Kozarich et al. |
| 5,385,915 A | 1/1995 | Buxbaum et al. |
| 5,391,723 A | 2/1995 | Priest |
| 5,434,050 A | 7/1995 | Maggio et al. |
| 5,442,043 A | 8/1995 | Fukuta et al. |
| 5,491,144 A | 2/1996 | Trinks et al. |
| 5,506,206 A | 4/1996 | Kozarich et al. |
| 5,525,727 A | 6/1996 | Bodor |
| 5,527,527 A | 6/1996 | Friden |
| 5,552,415 A | 9/1996 | May |
| 5,552,426 A | 9/1996 | Lunn et al. |
| 5,576,209 A | 11/1996 | Bredesen |
| 5,639,726 A | 6/1997 | Lawrence et al. |
| 5,663,336 A | 9/1997 | Trinks et al. |
| 5,703,129 A | 12/1997 | Felsenstein et al. |
| 5,817,626 A | 10/1998 | Findeis et al. |
| 5,876,948 A * | 3/1999 | Yankner ..................... 435/7.21 |
| 5,948,763 A | 9/1999 | Soto-Jara et al. |
| 6,172,043 B1 | 1/2001 | Ingram et al. |
| 2002/0004194 A1 * | 1/2002 | Lee et al. |

FOREIGN PATENT DOCUMENTS

| | | |
|---|---|---|
| WO | PCT/US96/10220 A1 | 12/1996 |
| WO | WO 98/30229 A1 | 7/1998 |
| WO | 98/30229 * | 7/1998 |

OTHER PUBLICATIONS

O'Dell, T. J. et al., "Long-Term Potentiation in the Hippocampus is Blocked by Tyosine Kinase Inhibitors," Nature vol. 353 (6344), (Sep. 1991) pp. 558–560.
Franco, R., et al., "Evidence for two Mechanisms of Amino Acid Osmolyte Release from Hippocampal Slices," Eur. J. Physiol. vol. 442 (Jun. 2001) pp. 791–800.
Dieter, M.Z., et al., "Tryphostin AG879, a Tyrosine Kinase Inhibaitor: Prevention of Transcriptional Activation of the Electrophile and Aromatic Hydrocarbon Response Elements," Biochemical Pharmacology, vol. 61(2) (Jan. 2001) pp. 215–225.
Anwer et al., Int, J. Pep. Protein Res. 36:392–399, 1990.
Arispb et al., Proc. Nat'l Acad. Sci. USA 90:10573–10577, 1993.
Arispb et al., Proc. Nat'l Acad. Sci. USA 90:567–571, 1993.
Blanchard et al., Brain Res 776(1–2):40–50, 1997.
Lam. Nature 354:82–84, 1991.
Levine, Protein Sci 2:404–410, 1993.
Mattson et al., J. Neurosci. 12:376–389, 1992.
Nachman et al., Regul. Pept. 57:359–370, 1995.
Rivera–Baeza et al., Neuropeptides 30:327–333, 1996.
Shen et al., Biophys J. 65:2383–2395, 1993.
Soto et al., Biochem. Biophys. Res. Commun. 226:672–680, 1996.
Spatola et al, Chemistry & Biochemistry of AA, Peptides & Proteins (Weinstein, Ed.) vol. 7, pp. 267–356, 1983.*
Tomski and Murphy, Arch. Biochem. Biophys. 294:630–638, 1992.
Blanchard et al., J. Alzheimer's Disease 2(2):137–149 (2000).

(Continued)

Primary Examiner—Bennett Celsa
(74) Attorney, Agent, or Firm—Wolf, Greenfield & Sacks, P.C.

(57) ABSTRACT

The invention involves identification of a mechanism of β-amyloid peptide cytotoxicity, which enables treatment of conditions caused by β-amyloid peptide aggregates by administration of compounds which antagonize the mechanism of cytotoxicity. The invention includes the identification and isolation of compounds which can antagonize the aggregation of β-amyloid peptides and the neurotoxic effects of such aggregates. The compounds include isolated peptides which were selected for their ability to form a complex with a β-amyloid peptide, or are derived from peptides so selected. Methods for treating conditions resulting from neurotoxic β-amyloid peptide aggregates and pharmaceutical preparations are provided. Also provided are methods for selecting additional compounds which can antagonize the aggregation of β-amyloid peptides and the neurotoxic effects of such aggregates.

10 Claims, 18 Drawing Sheets

OTHER PUBLICATIONS

Brauner et al., *Biochim Biophys Acta* 1984 Apr. 11; 771(2):208–16.
Cooper et al., Biochemistry. 29:3859–3865 (1990).
Durell et al., *Biophys. J.* 67:2137–2145 (1994).
Hartinger, *J. Biol. Chem.* 268:23122–23127 (1993).
Hartley et al., *J. Neuroscience* 19:8876–8884 (1999).
Kawahara et al., *Biophys. J.* 73:67–75 (1997).
Langheinrich, et al., *J. Physiol.* 502 (Pt 2):397–408 (1997).
Pollard et al., *Ann. N.Y. Acad. Sci.* 695:165–168 (1993).
Sanderson et al., *Brain Res.* 744:7–14 (1977).
Walsh et al., *J. Biol. Chem.* 274:25945–52 (1999).
Yankner et al., *Science.* 250:279–282 (1990).

* cited by examiner

*Fig. 11*  Aβ1-42 -/+ CNQX

*Fig. 12*  TRIS blocking

Fig. 14   TTX

Fig. 15  Tyr/0Ca

METHODS FOR IDENTIFYING TREATMENTS FOR NEUROTOXICITY IN ALZHEIMER'S DISEASE CAUSED BY β-AMYLOID PEPTIDES

RELATED APPLICATIONS

This application is a continuation-in-part of U.S. application Ser. No. 9/005,215, filed Jan. 9, 1998, now U.S. Pat. No. 6,172,043, which is a continuation of U.S. application Ser. No. 08/960,188, filed Oct. 29, 1997, now abandoned, which application claims priority under 35 U.S.C. §119 from U.S. provisional application Ser. No. 60/035,847, filed Jan. 10, 1997.

FIELD OF THE INVENTION

The invention relates to compounds which antagonize the neurotoxic effects of β-amyloid peptide aggregates, methods for using such compounds and methods for discovering compounds which also antagonize the neurotoxic effects of β-amyloid peptide aggregates.

BACKGROUND OF THE INVENTION

The post-mortem pathology of Alzheimer's Disease is characterized by the presence in particular regions of the brain of many extracellular plaques and of many intracellular neurofibrillary tangles, whose density correlates with the severity of dementia. There is also massive, but regional, neuronal cell disfunction and cell loss, caused presumably by the reported neurotoxicity of the β-amyloid peptides (also referred to herein as βAP and Aβ) which are components of senile plaques. The cytotoxicity of the β-amyloid peptides was first established in primary cell cultures from rodent brains and also in human cell cultures. These were relatively long-term experiments, lasting for a few days. The immediate molecular cause of the cytotoxicity was not clear from these reports. The work of Mattson et al. (J. Neurosci. 12:376–389, 1992) indicates that β-amyloid peptides, including the sequence $βAP_{25-35}$, in the presence of the excitatory neurotransmitter glutamate causes an immediate increase in intracellular calcium, which, it is supposed, is very toxic to the cell through its greatly increased second messenger activities.

The formation of pathological β-amyloid peptides in Alzheimer's Disease is not well understood. The amyloid precursor protein (APP) is a very large transmembrane protein whose normal turnover degradation cleaves the presumptive β-amyloid peptide in the middle, thus making it inactive as a neurotoxic agent. In addition, the future C-terminus of β-amyloid peptides is buried in the middle of the lipid membrane. How the degradation of APP is altered in Alzheimer's Disease (AD) is only gradually becoming clear with no convincing explanation at present.

There are three β-amyloid peptides, $βAP_{1-42}$, $βAP_{1-40}$, and $βAP_{25-35}$ (also referred to herein as Aβ1-42, Aβ1-40 and Aβ25-35, respectively), which are homologous to the tachykinin neuropeptides. All three peptides are strongly neurotoxic when applied to cultured cells. $βAP_{1-40}$ and $βAP_{1-42}$ are the most prominent components of senile plaques. It is not clear whether $βAP_{25-35}$ occurs in the brains of AD individuals. $βAP_{25-35}$ might be absent because it has been scavenged when dead neurons are removed.

The $βAP_{1-42}$ peptide, and related shorter peptides, are cytotoxic towards cultured neuronal cells at micromolar concentrations, but neurotrophic at nanomolar concentrations.

Others have observed that the peptide is cytotoxic also in vivo. Variability in results from different laboratories perhaps can be ascribed to the different propensities of particular β-amyloid peptides to aggregate in aqueous solution. It has been suggested that long-term cytotoxicity resides in insoluble aggregates. The molecular mechanism of this cytotoxicity is not well known, perhaps because most of the reported experiments examine chronic cytotoxic effects only after 24–48 hours of exposure to insoluble aggregates of β-amyloid peptides.

The ability of β-amyloid peptides such as $βAP_{1-40}$ to form cation-selective ionophores was postulated earlier as a mechanism for cytotoxicity (Arispe et al., Proc. Nat'l Acad. Sci. USA 90:10573–10577, 1993; Arispe et al., Proc. Nat'l Acad. Sci. USA 90:567–571, 1993). However, these experiments were carried out in artificial membranes. While in actual cells the ionophore mechanism might indeed be an important factor, there are at least two other mechanisms: interaction between the β-amyloid peptides with existing ion channels, and penetration of the peptides into the cell with consequent release of calcium from internal stores.

Thus, while the precise mechanism of neurotoxicity of β-amyloid peptides in Alzheimer's Disease has not been definitively established, there is a need to determine which of the aforementioned mechanisms of cytotoxicity is the cause of neuronal cell death in AD. Identification of the cytotoxic mechanism is needed to enhance the prospects of designing compounds capable of antagonizing the effects of aggregation of β-amyloid peptides.

SUMMARY OF THE INVENTION

The invention involves in one aspect identification of a mechanism of β-amyloid peptide cytotoxicity, which enables treatment of conditions caused by β-amyloid peptide aggregates by administration of compounds which antagonize the mechanism of cytotoxicity. The invention involves in another aspect the identification and isolation of peptides which can antagonize the aggregation of β-amyloid peptides and the neurotoxic effects of such aggregates. The isolated peptides include decoy peptides which were selected for their ability to form a complex with $βAP_{25-35}$, or are derived from peptides so selected. The decoy peptides have considerable β-sheet forming potential. Decoy peptides associate with the multimer-forming β-amyloid peptide and either block the usual aggregation or are incorporated into the multimer peptide (aggregate) to make it inactive. The invention further involves the use of such compounds in the preparation of a medicament for preventing cytotoxicity resulting from β-amyloid peptide aggregation.

According to another aspect of the invention, a composition is provided. The composition includes a decoy peptide which binds to a neurotoxic β-amyloid peptide and reduces the ability of the neurotoxic β-amyloid peptide to form aggregates which increase calcium influx into neuronal cells, preferably NT2-N cells differentiated with retinoic acid. Preferably the decoy peptide is non-hydrolyzable, particularly a decoy peptide selected from the group consisting of peptides comprising D-amino acids, peptides comprising a -psi[CH₂NH]— reduced amide peptide bond, peptides comprising a -psi[COCH₂]— ketomethylene peptide bond, peptides comprising a -psi[CH(CN)NH]— (cyanomethylene)amino peptide bond, peptides comprising a -psi[CH₂CH(OH)]— hydroxyethylene peptide bond, peptides comprising a -psi[CH₂O]— peptide bond, and peptides comprising a -psi[CH₂S]— thiomethylene peptide bond. In other embodiments, the decoy peptide binds to a neurotoxic β-amyloid peptide is selected from the group consisting of $\beta AP_{1-42}$ and $\beta AP_{25-35}$. Preferably, the decoy peptide has β-sheet forming potential, and is between 4 and 20 amino acids in length. More preferably, the decoy peptide is between 5 and 10 amino acids in length. Optionally, the decoy peptide can be a cyclized peptide.

In certain preferred embodiments, the decoy peptide comprises a sequence selected from the group consisting of amino acids 1–6 of SEQ ID NO: 1, amino acids 1–6 of SEQ ID NO:2, amino acids 1–6 of SEQ ID NO:3, amino acids 1–6 of SEQ ID NO:4, amino acids 1–6 of SEQ ID NO:5, amino acids 16 of SEQ ID NO:6, amino acids 1–6 of SEQ ID NO:7, amino acids 1–6 of SEQ ID NO:8, amino acids 1–9 of SEQ ID NO:9, amino acids 1–7 of SEQ ID NO:12, amino acids 1–7 of SEQ ID NO:13, amino acids 1–7 of SEQ ID NO: 14, amino acids 1–6 of SEQ ID NO:15, amino acids 1–5 of SEQ ID NO:16, amino acids 1–9 of SEQ ID NO:17, amino acids 1–9 of SEQ ID NO:18, amino acids 1–7 of SEQ ID NO:19, amino acids 1–5 of SEQ ID NO:21, amino acids 1–5 of SEQ ID NO:22, amino acids 1–5 of SEQ ID NO:23, amino acids 1–5 of SEQ ID NO:24, amino acids 1–5 of SEQ ID NO:25, amino acids 1–5 of SEQ ID NO:26, amino acids 1–5 of SEQ ID NO:27, amino acids 1–6 of SEQ ID NO:28, amino acids 1–6 of SEQ ID NO:29, and amino acids 1–6 of SEQ ID NO:30. In particularly preferred embodiments, the the decoy peptide comprises a sequence selected from the group consisting of amino acids 1–6 of SEQ ID NO:2, amino acids 1–6 of SEQ ID NO:9 and amino acids 1–9 of SEQ ID NO:17.

According to another aspect of the invention, the decoy peptides of the invention are conjugated to a compound which facilitates transport across the blood-brain barrier into the brain. Preferably, the compound is selected from the group consisting of a transferrin receptor binding antibody, cationized albumin, Met-enkephalin, lipoidal forms of dihydropyridine, cationized antibodies, and naturally occurring fatty acids.

According to another aspect of the invention, a method for treating a subject having a condition characterized by neurotoxic β-amyloid peptide aggregates is provided. The method involves administering to the subject an amount of a decoy peptide, which binds to a neurotoxic β-amyloid peptide such as $\beta AP_{1-42}$, $\beta AP_{1-40}$, or $\beta AP_{25-35}$ and reduces the ability of the neurotoxic β-amyloid peptide to form aggregates which increase calcium influx into neuronal cells, effective to reduce neurotoxic β-amyloid peptide aggregates in the subject. In certain embodiments, the decoy peptide is conjugated to a compound which facilitates transport across the blood-brain barrier into the brain. In other embodiments, the method comprises administering a compound which increases transport across the blood-brain barrier.

According to a further aspect of the invention, a method for reducing β-amyloid peptide induced increased neuronal cell calcium influx in a subject is provided. The method involves administering to the subject an amount of a compound effective to reduce neurotoxic β-amyloid peptide aggregate-induced neuronal cell calcium influx. In one embodiment, the compound is a decoy peptide which binds to a neurotoxic β-amyloid peptide and reduces the ability of the neurotoxic β-amyloid peptide to increase calcium influx into neuronal cells. Included are decoy peptides which are conjugated to, or administered with, a compound which facilitates transport of the decoy peptide across the blood-brain barrier into the brain. In other embodiments, the compound is a non-NMDA channel antagonist. Combinations of the foregoing compounds can be administered together.

According to still another aspect of the invention, a pharmaceutical composition is provided. The pharmaceutical composition includes a decoy peptide which binds to a neurotoxic β-amyloid peptide and reduces the ability of the neurotoxic β-amyloid peptide to form aggregates which increase calcium influx into neuronal cells and a pharmaceutically-acceptable carrier. The decoy peptide is present in an amount effective to decrease or inhibit the formation of neurotoxic β-amyloid peptide aggregates in the subject. The decoy peptide can be conjugated to a compound which facilitates transport of the decoy peptide across the is blood-brain barrier into the brain. In other embodiments, the pharmaceutical composition can include a non-NMDA channel antagonist. The invention thus also contemplates specifically the use of the decoy peptides of the invention and/or the use of a non-NMDA channel antagonist in the manufacture of a medicament for treating conditions characterized by unwanted calcium influx resulting from neurotoxic β-amyloid peptide aggregates. Any of the foregoing embodiments can include a compound which increases transport across the blood-brain barrier.

According to another aspect of the invention, a method for identifying lead compounds for a pharmacological agent useful in the treatment of disease associated with β-amyloid peptide aggregation is provided. The method involves first forming a mixture comprising a β-amyloid peptide containing a β-sheet forming domain, a decoy peptide which binds to a neurotoxic β-amyloid peptide, and a candidate pharmacological agent. The method further involves incubating the mixture under conditions which, in the absence of the candidate pharmacological agent, permit a decoy peptide to selectively bind the neurotoxic β-amyloid peptide. Selective binding of the neurotoxic β-amyloid peptide by the decoy peptide is then detected. A reduction of selective binding indicates that the candidate pharmacological agent is a lead compound for a pharmacological agent which disrupts β-amyloid peptide aggregation. Preferably, the candidate pharmacological agent is a peptide or a small organic molecule, such as a molecule prepared by combinatorial chemistry.

According to yet a further aspect of the invention, a method for identifying lead compounds for a pharmacological agent useful in the treatment of disease associated with increased neuronal cell calcium influx induced by the presence of β-amyloid peptide aggregates is provided. A neuronal cell is provided in which calcium influx may be detected. The neuronal cell preferably is loaded with a calcium-sensitive compound which is detectable in the presence of calcium. A mixture including neurotoxic β-amyloid peptide containing a β-sheet forming domain and a candidate pharmacological agent is formed, and the mixture is incubated under conditions which, in the absence of the candidate pharmacological agent, permit the β-amyloid peptide to aggregate and cause a first amount of calcium influx into the cell. The neuronal cell is contacted with the mixture under conditions which permit influx of a test amount of calcium into the neuronal cell if neurotoxic β-amyloid aggregates are present. Calcium influx then is detected. For example, in the preferred embodiment, a calcium-sensitive compound is then detected as a measure of the presence of calcium in the neuronal cell. if the test amount of calcium is less than the first amount, then the candidate pharmacological agent is a lead compound for a pharmacological agent which disrupts the neurotoxic effects of β-amyloid peptide aggregation. In preferred embodiments, the candidate pharmacological agent is a peptide, non-NMDA channel antagonist, or a small organic molecule.

In another aspect of the invention, methods for identifying lead compounds for a pharmacological agent useful in the treatment of conditions associated with increased neuronal cell calcium influx induced by the presence of β-amyloid peptide (Aβ) aggregates are provided. The methods include providing a neuronal cell loaded with a calcium-sensitive compound which is detectable in the presence of calcium and contacting the neuronal cell with Aβ aggregates under conditions which permit calcium influx into the neuronal cell. The calcium-sensitive compound is detected as a measure of calcium influx induced by Aβ aggregates. The methods also provide contacting the neuronal cell with a candidate pharmacological agent, and detecting the calcium-sensitive compound as a measure of the relative presence of calcium in the neuronal cell induced by the candidate pharmacological agent. Detection of a lesser amount of calcium in the neuronal cell than is present when the neuronal cell is contacted with Aβ aggregates indicates that the candidate pharmacological agent is a lead compound for a pharmacological agent which reduces Aβ aggregate induced neuronal cell calcium influx. In certain embodiments, the candidate pharmacological agent is a peptide, a non-NMDA channel antagonist, or a small organic molecule.

According to a further aspect of the invention, methods for identifying lead compounds for a pharmacological agent useful in the treatment of conditions associated with increased neuronal depolarization induced by the presence of β-amyloid peptide (Aβ) aggregates. The methods include providing a neuronal cell in a medium containing a potentiometric compound, wherein the influx into the neuronal cell of the potentiometric compound upon depolarization of the neuronal cell is detectable, forming a mixture comprising a Aβ containing a β-sheet forming domain, and a candidate pharmacological agent, and incubating the mixture under conditions which, in the absence of the candidate pharmacological agent, permit the Aβ to aggregate. The methods also include contacting the neuronal cell with the mixture, under conditions which, in the presence of Aβ aggregates, permit influx of a control amount of the potentiometric compound into the neuronal cell, and detecting the potentiometric compound as a measure of the relative depolarization of the neuronal cell. Detection of a lesser amount of potentiometric compound in the neuronal cell than is present when the neuronal cell is contacted with Aβ aggregates indicates that the candidate pharmacological agent is a lead compound for a pharmacological agent which disrupts Aβ aggregation. In certain embodiments, the candidate pharmacological agent is a peptide or a small organic molecule. In other embodiments, the potentiometric compound is fluorescent; preferably the potentiometric compound is bis-(1,3-dibutylbarbituric acid)trimethine oxonol (DiBAC$_4$(3)).

According to still another aspect of the invention, methods for identifying lead compounds for a pharmacological agent useful in the treatment of conditions associated with increased neuronal depolarization induced by the presence of β-amyloid peptide (Aβ) aggregates are provided. The methods include providing a neuronal cell in a medium containing a potentiometric compound, wherein the influx into the neuronal cell of the potentiometric compound upon depolarization of the neuronal cell is detectable, contacting the neuronal cell with Aβ aggregates under conditions which permit influx of a control amount of the potentiometric compound into the neuronal cell, and detecting the potentiometric compound in the neuronal cell as a measure of depolarization induced by Aβ aggregates. The methods also include contacting the neuronal cell with a candidate pharmacological agent, and detecting the potentiometric compound in the neuronal cell as a measure of the relative depolarization of the neuronal cell in the presence of the candidate pharmacological agent. Detection of a lesser amount of potentiometric compound in the neuronal cell than is present when the neuronal cell is contacted with Aβ aggregates but not the candidate pharmacological agent indicates that the candidate pharmacological agent is a lead compound for a pharmacological agent which reduces Aβ aggregate induced neuronal cell depolarization. In certain embodiments, the candidate pharmacological agent is a peptide or a small organic molecule. In other embodiments, the potentiometric compound is fluorescent; preferably the potentiometric compound is bis-(1,3-dibutylbarbituric acid) trimethine oxonol (DiBAC$_4$(3)).

These and other objects and features of the invention are described in greater detail below.

DETAILED DESCRIPTION OF THE DRAWINGS

FIG. 1 contains graphs which show the changes in internal $Ca^{2+}$ over time in hNT cells in response to $\beta AP_{25-35}$, and $\beta AP_{1-42}$. FIGS. 1A and 1B are bar graphs which depict the mean $Ca^{2+}$ influx, and FIGS. 1C and 1D are histograms which depict the $Ca^{2+}$ influx in individual cells.

FIG. 9 shows the effect of decoy peptides on the aggregation kinetics of $\beta AP_{1-42}$ and $\beta AP_{25-35}$. FIG. 9A shows the aggregation rate of $\beta AP_{1-42}$. FIG. 9B shows the aggregation rate of $\beta AP_{1-42}$ in the presence of DP16. FIG. 9C shows the aggregation rate of $\beta AP_{25-35}$. FIG. 9D shows the aggregation rate of $\beta AP_{25-35}$ in the presence of DP8. FIG. 9E shows the aggregation rate of $\beta AP_{25-35}$ in the presence of DP16.

Figure 10:
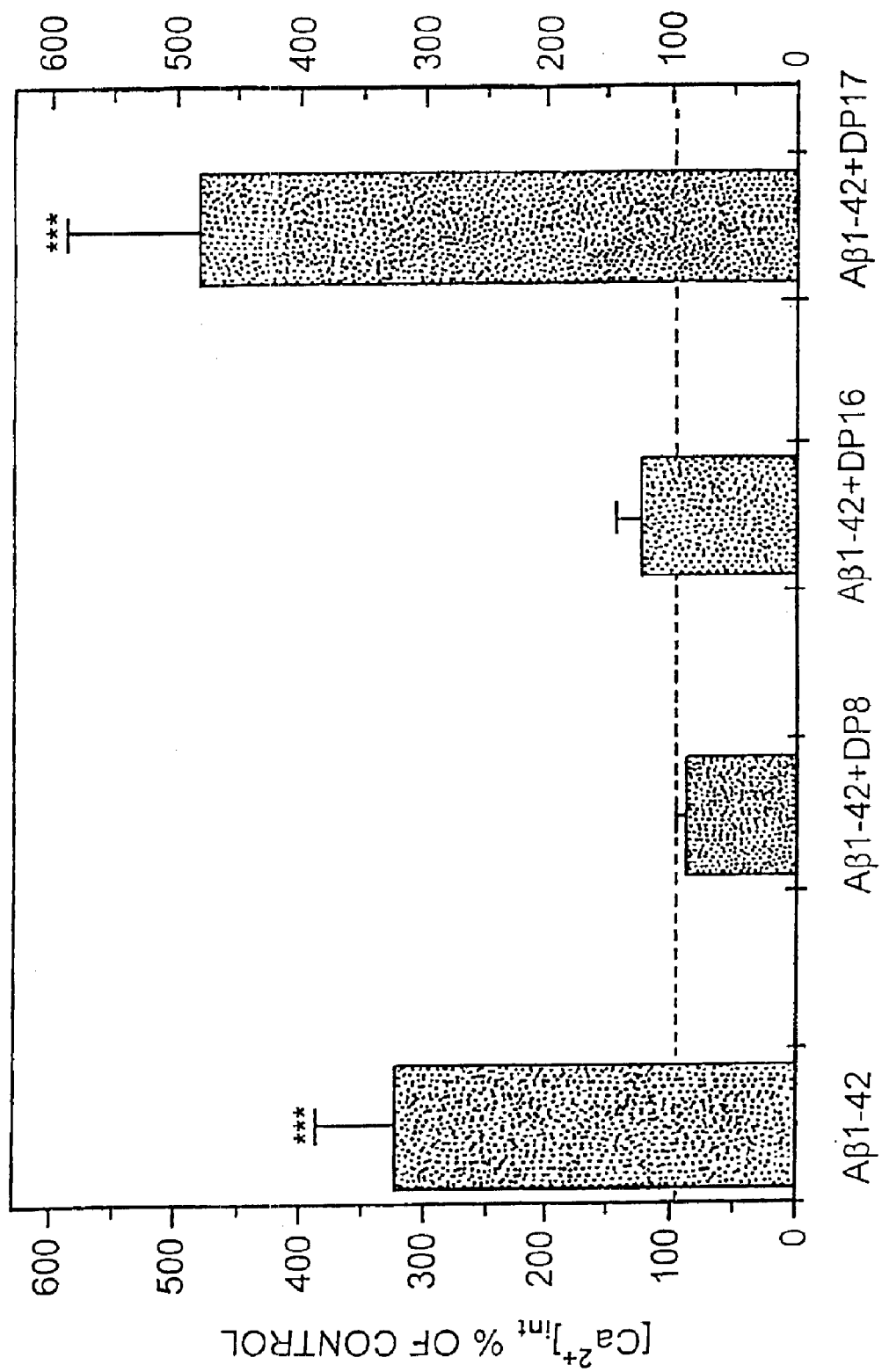

FIG. 10 is a bar graph which shows that decoy peptides can reduce the $\beta AP_{1-42}$-induced $Ca^{2+}$ influx.

Figure 11:
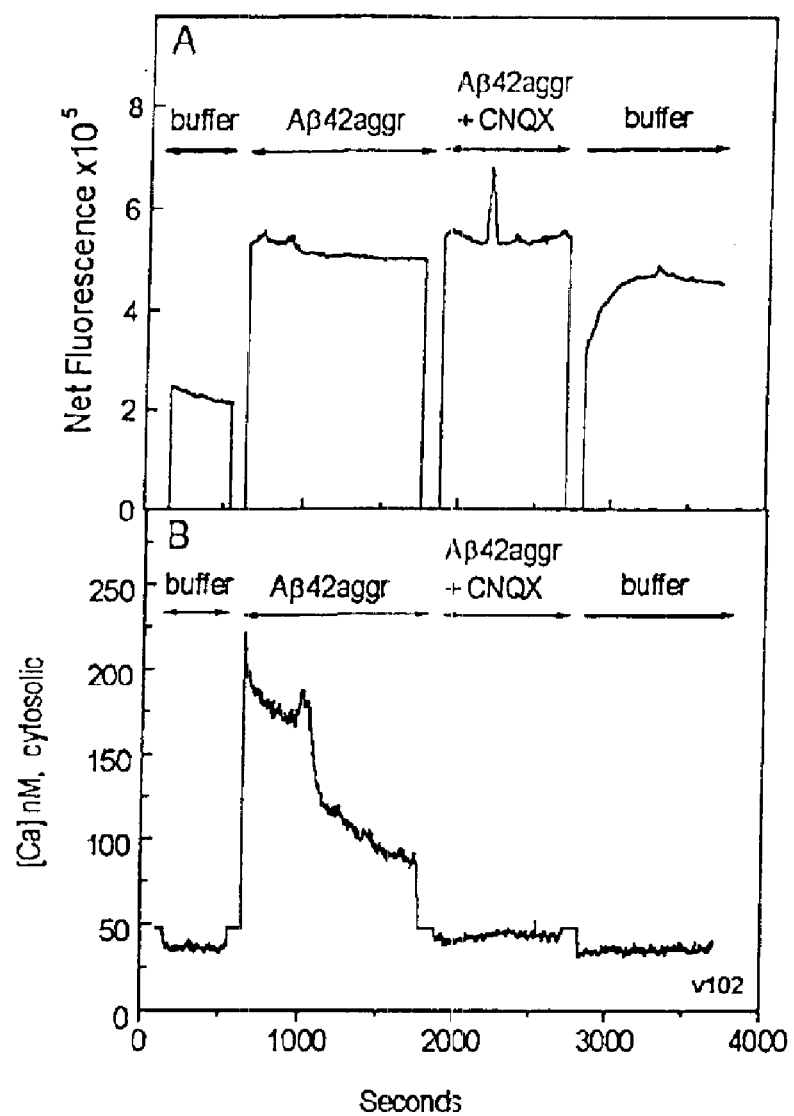

FIG. 11 shows that aggregated Aβ1-42 causes large membrane depolarization (A) and large calcium influx; and shows the effect of CNQX. (A) Fluorescence of the DiBAC$_4$(3) rose rapidly to a high plateau. The presence of CNQX; and replacing the buffer with Tyrode's/2Ca did not significantly change fluorescence. (B) Fluorescence of the ratiometric Ca dye fura-2 was converted to cytosolic calcium concentrations. In the presence of the aggregated Aβ1-42 there is a large increase in cytosolic calcium which spontaneously desensitizes to a level ~200% of control. Addition of CNQX lowers the remaining calcium level to the original control value.

Figure 12:
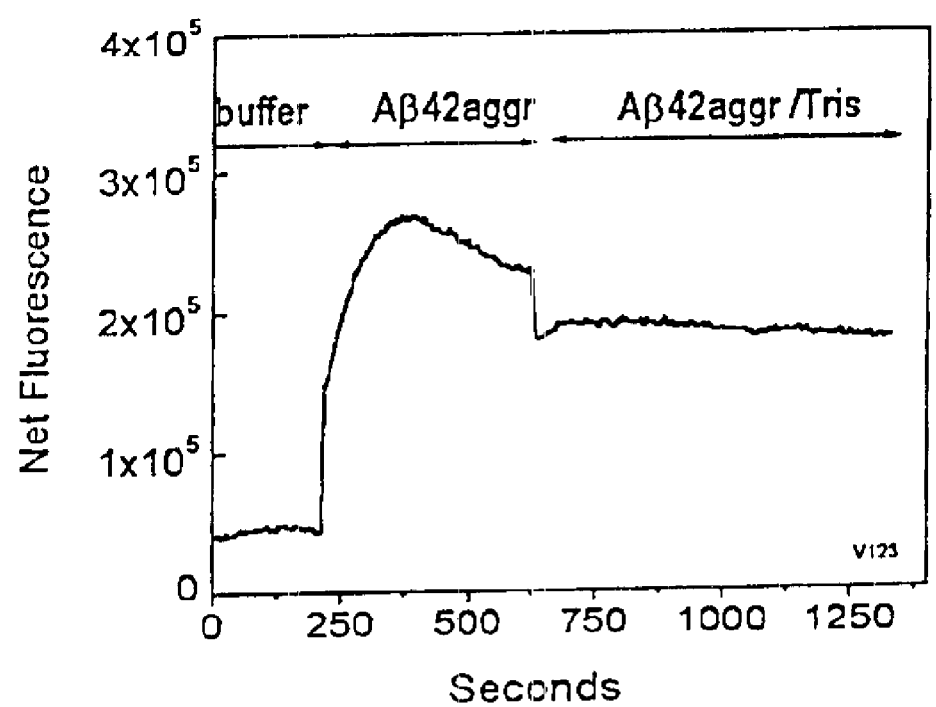

FIG. 12 shows that tromethamine [TRIS$^+$] partially blocks membrane depolarization. hNT neuronal cells were exposed to aggregated 20 µMAβ1-42 followed by Aβ1-42 plus 10 mM TRIS+. The Tyrode's/2Ca buffer contained 100 nM DiBAC$_4$(3).

Figure 13:
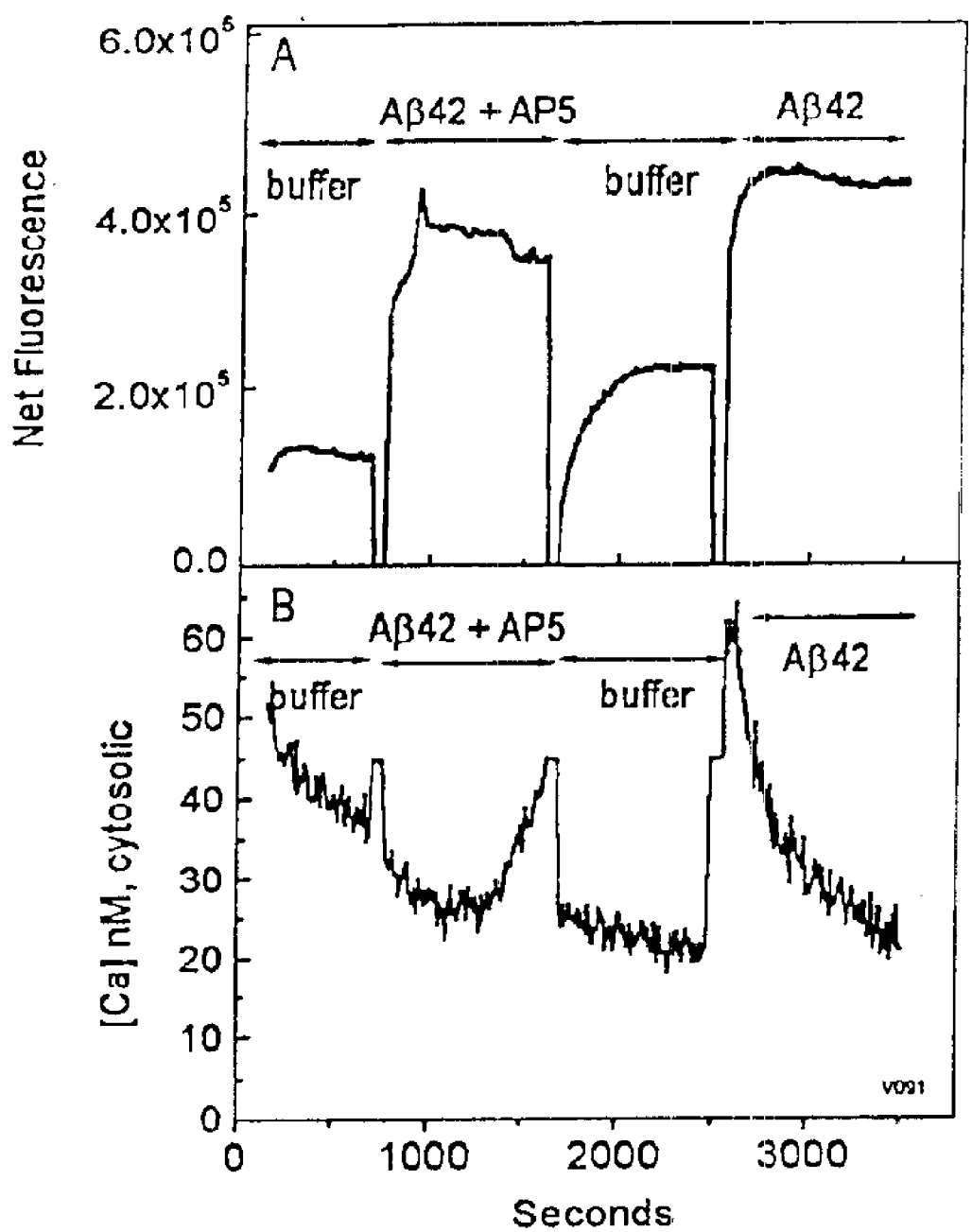

FIG. 13 shows that D-AP5, an NMDA receptor antagonist, does not block membrane depolarization by aggregated Aβ1-42 (A); but does inhibit calcium influx (B). hNT neuronal cells were exposed to aggregated 20 µM Aβ1-42 for ~1,000 sec, exchanged for Tyrode's/2Ca, which was replaced with aggregated Aβ1-42 (20 µM). Depolarization was measured with DiBAC$_4$(3), and cytosoloic calcium with fura-2.

Figure 14:
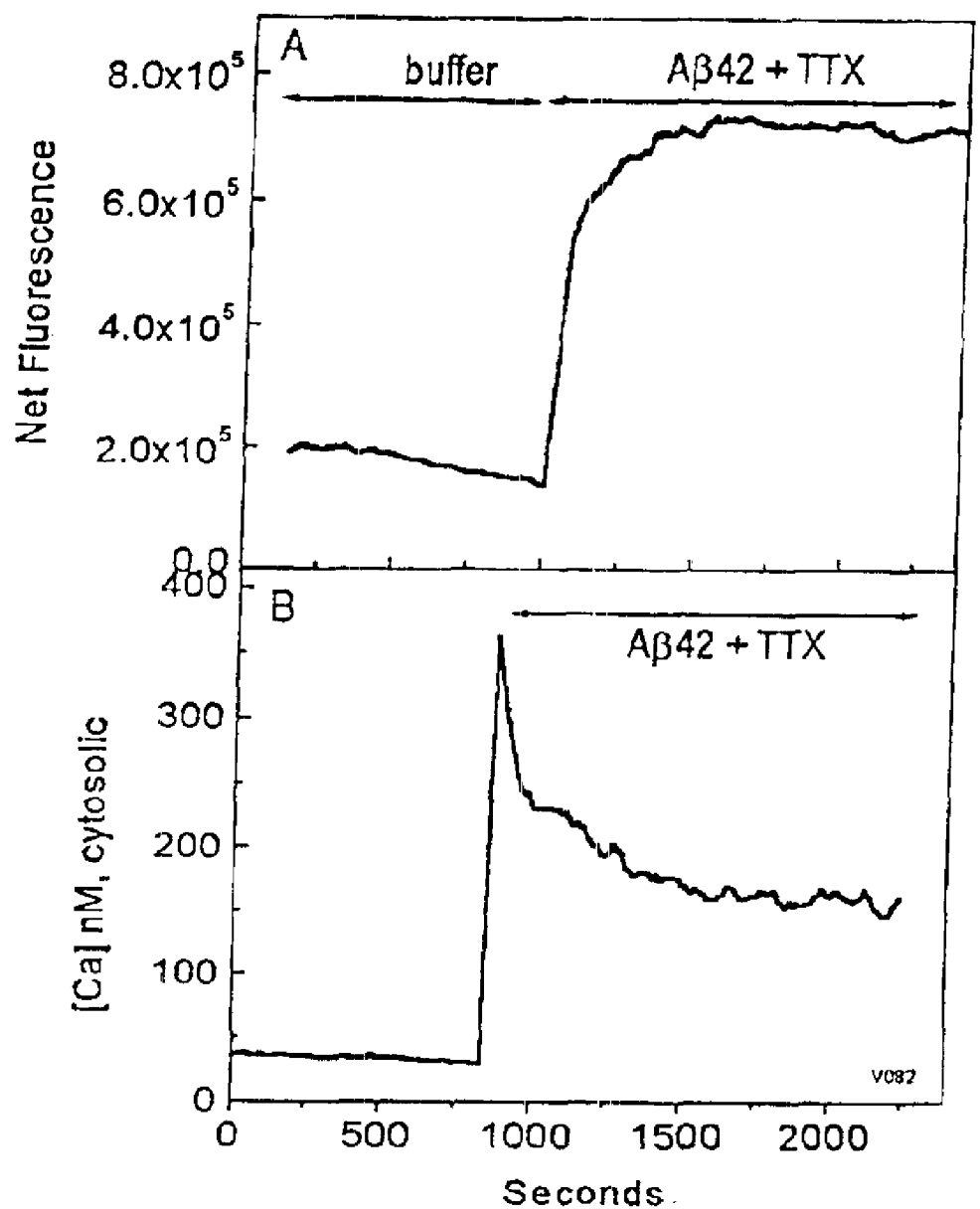

FIG. 14 is a graph depicting the effect of the presence of 1 µM tetrodotoxin (TTX), a specific sodium ion channel blocking agent, that allows both membrane depolarization (A) as measured by 100 nM DiBAC$_4$(3), and the rise in cytosolic calcium (B), as measured by fura-2, when aggregated 20 µM Aβ1-42 is added to hNT neuronal cells.

Figure 1A:
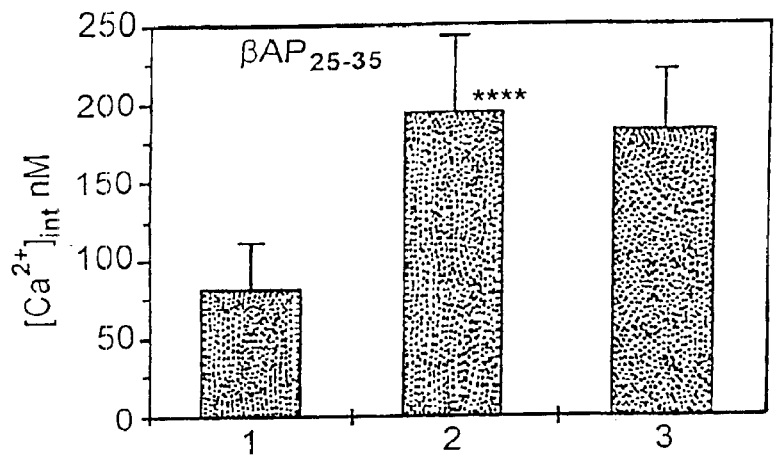
Figure 1B:
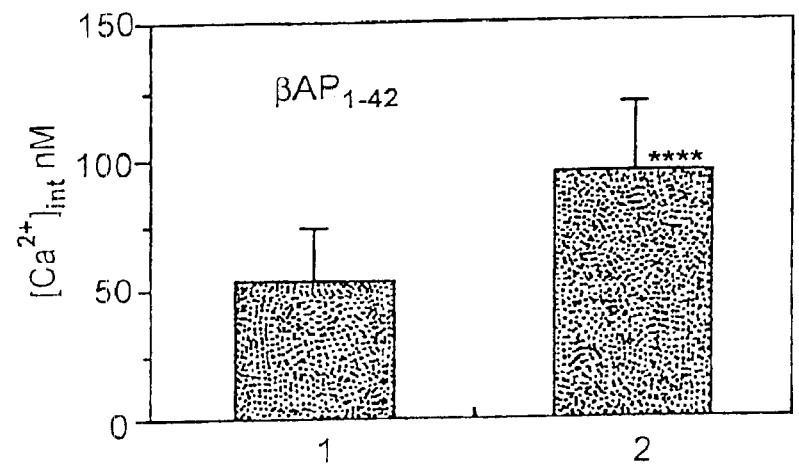
Figure 1C:
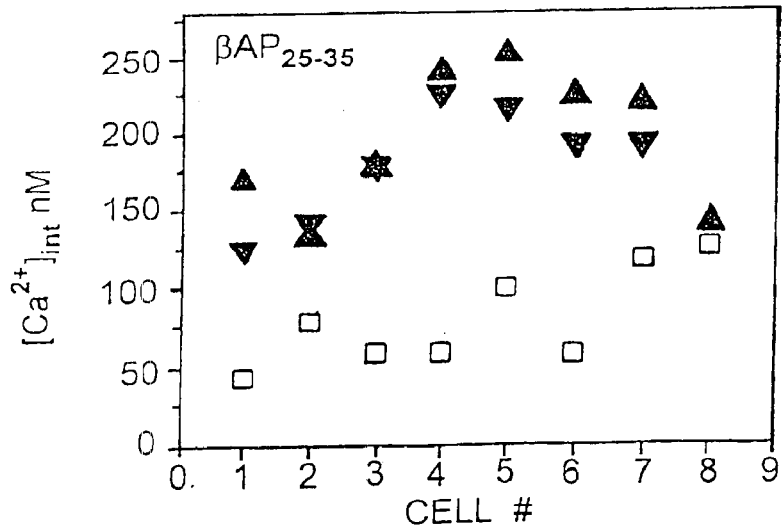
Figure 1D:
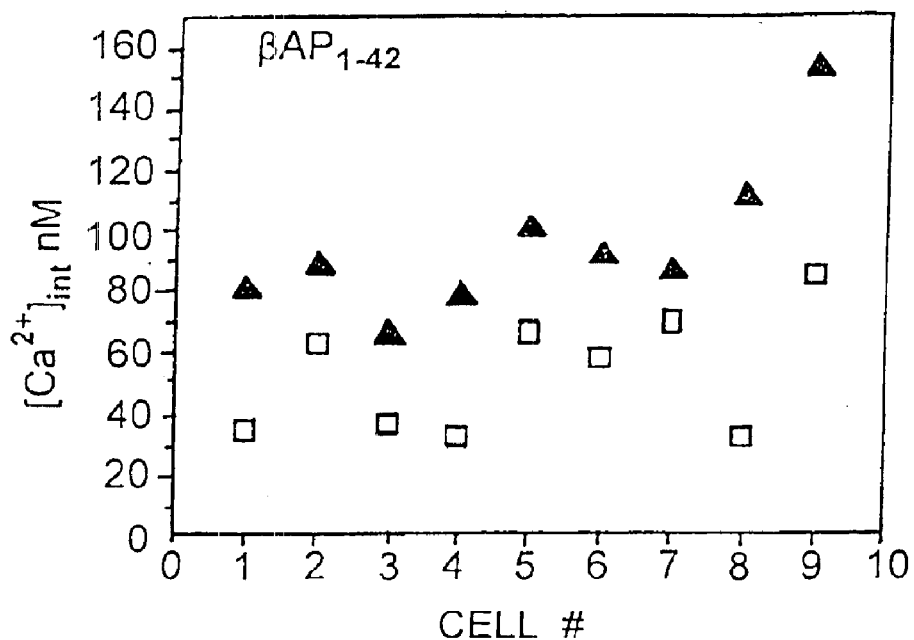
Figure 15:
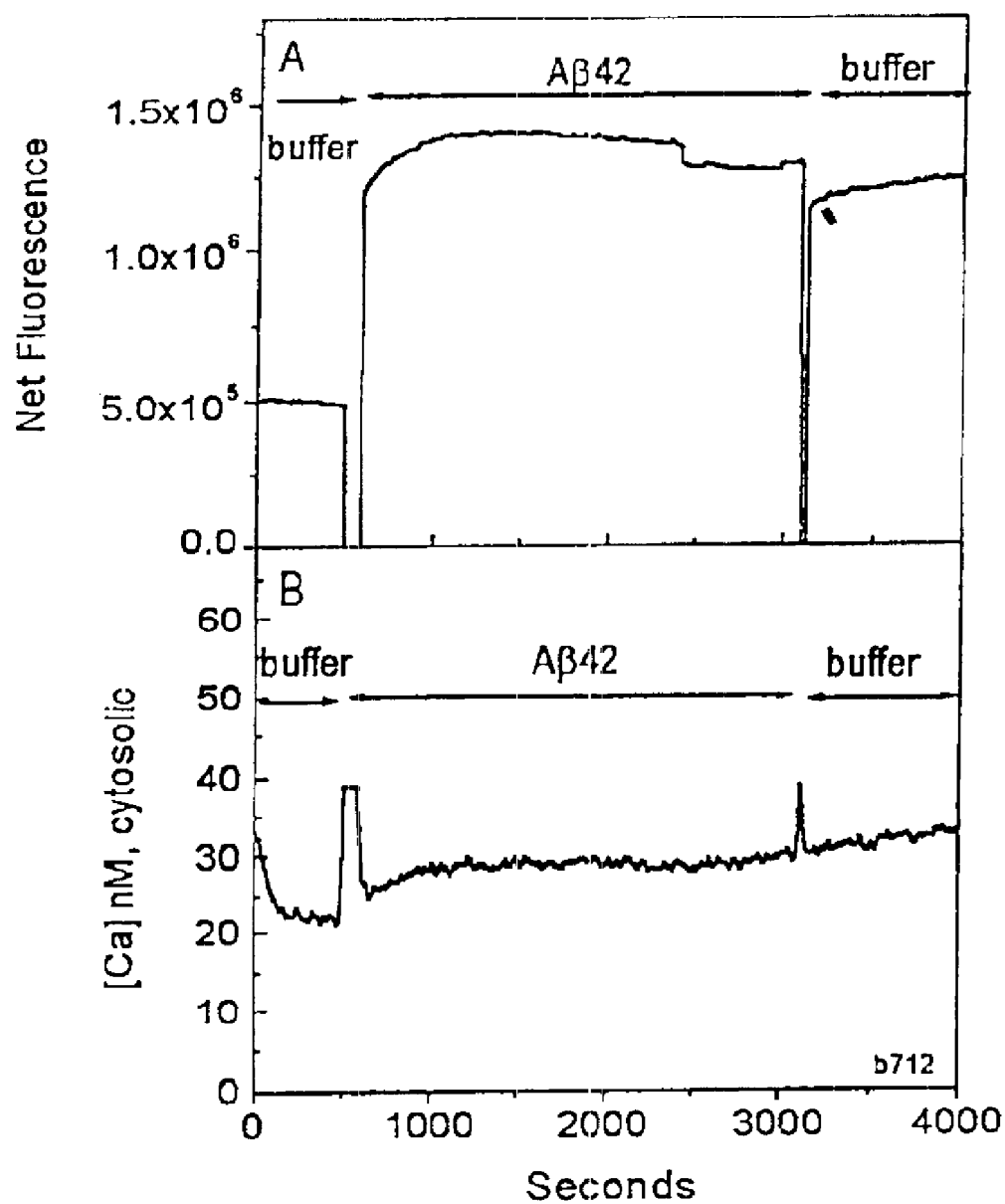

FIG. 15 shows the aggregated Aβ1-42 causes large membrane depolarization even when there is no calcium in the external solution. The hNT cells were exposed to aggregated Aβ1-42 in Tyrode's medium without calcium. (A) The expected greatly increased membrane depolarization was observed as a plateau, lasting for ~2,500 seconds. (B) There was almost no rise in cytosolic calcium indicating that the increase observed in FIG. 1B was due to calcium influx.

Figure 16:
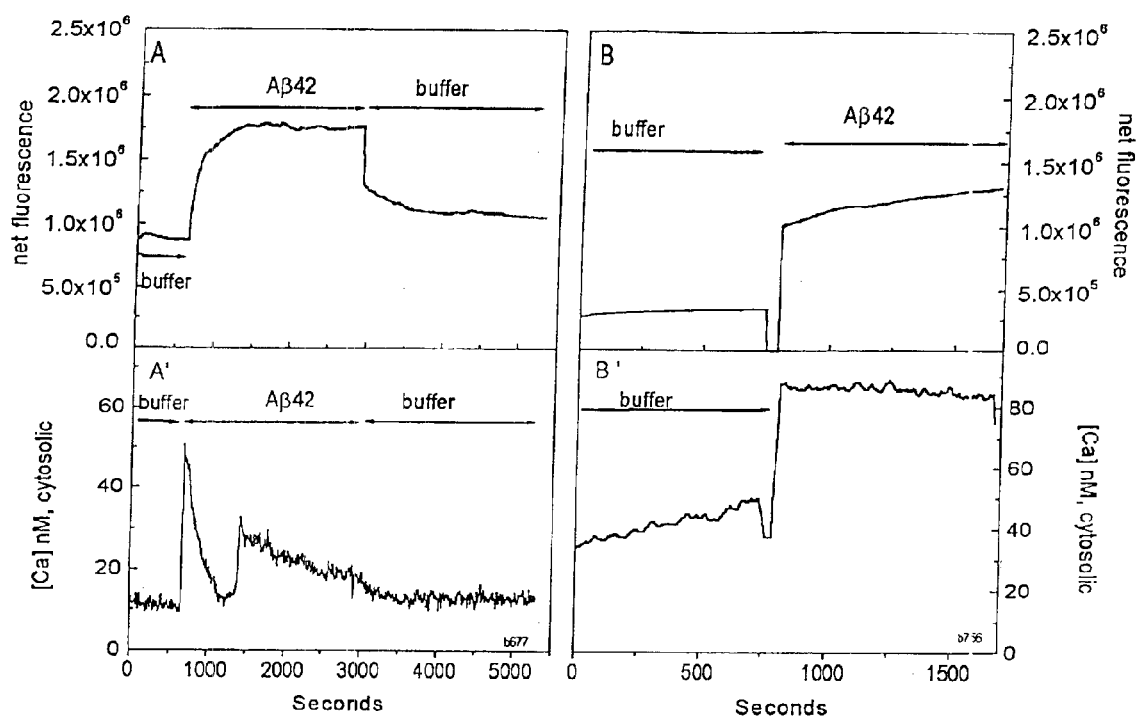

FIG. 16 indicates that sodium, the principal cation in the external buffer, can be replaced by the large cations TEA+ and NMDG+. (A) and (B) show the changes in fluorescence of the voltage-sensitive dyd DiBAC$_4$(3) and (A') and (B') show changes in cytosolic calcium concentration, as measured by fura-2. (A) Replacing the external sodium ions with an equal concentration [150 mM] also allows a large and lasting membrane depolarization when aggregated Aβ1-42 is added to hNT cells. This is only partially reversed when the peptide solution is replaced with Tyrode's/2Ca. (A') The expected sharp increase in cytosolic calcium also occurs, followed by desensitization. The sharp dip and recovery of calcium levels is only seen in some experiments. (B) When Na+ in the external Tyrode's solution was replaced by the impermeant N-methyl-D-glucamine+, membrane depolarization in the presence of aggregated Aβ1-42 was observed as usual. (B') Cytosolic calcium also rises when aggregated Aβ1-42 is added.

DETAILED DESCRIPTION OF THE INVENTION

We have chosen the peptides βAP$_{25-35}$ (GSNKGAIIGLM, SEQ ID NO:10) and βAP$_{1-42}$ (Aβ1-42; SEQ ID NO:20) as model systems to explore the effect of β-amyloid peptides on calcium homeostasis in neuronal cells, using quantitative estimation of the internal calcium concentration of the cells.

Reports in the literature have shown that β-amyloid peptides cause an influx of calcium into cells, using not only βAP$_{25-35}$, but also βAP$_{1-40}$ and βAP$_{1-42}$ We have investigated the connection between β-amyloid peptide aggregation and the influx of calcium into neuronal cells as the first molecular event in the cytotoxicity of neurons in Alzheimer's Disease.

Pollard has reported the formation of ionophores from βAP$_{1-40}$ in artificial membrane which could be blocked by AlCl$_3$ or Tromethamine (Arispe, 1993). Our attempts to reproduce aluminum blockage in our experiments have been inconclusive because we found that AlCl$_3$ by itself powerfully induces calcium influx in hNT neuronal cells from external calcium sources. Thus, we turned to an alternative hypothesis, that aggregates of the β-amyloid peptides modulate ligand-gated ion channels such as NMDA and non-NMDA channels. Previous patch-clamp experiments indicated that voltage-gated calcium channels were not involved, because CdCl$_2$ did not block the calcium influx. We have also determined that the increased cytosolic calcium is derived entirely from the external medium. We have determined that calcium influx into hNT neuronal cells caused by βAP$_{25-35}$ can be blocked by MgCl$_2$, and by CNQX, but not by DL-AP5. hNT neuronal cells are known to express both NMDA and non-NMDA glutamate receptor channels. The blocking effect of CNQX, coupled with the lack of blocking effect of DL-AP5, indicated that the effect on calcium influx by βAP$_{25-35}$ aggregates in hNT cells is mediated by a non-NMDA cation channel. Since these observations involved the obligatory role of β-amyloid peptide aggregates, we hypothesized that compounds capable of antagonizing the formation of βAP$_{1-42}$ or βAP$_{25-35}$ aggregates will alleviate neurotoxicity of Alzheimer's Disease. These observations also suggest a strategy for developing therapeutics which modulate the activity of non-NMDA channels affected by β-amyloid peptide aggregates.

Peptides with a relatively high content of β-sheet forming sequence are likely to form multimers or aggregates, often in the form of fibrils, in aqueous solutions. Such β-sheet forming sequences are often present in intact globular proteins, but are embedded in other largely hydrophilic amino acid sequences and thus the proteins are kept in solutions. Once released from their precursor protein by proteolysis, peptides with β-sheet forming sequences can aggregate. Relevant to Alzheimer's Disease is the "abnormal" proteolysis of APP (Amyloid Precursor Protein) which yields βAP$_{1-40}$, βAP$_{1-42}$, and possibly also βAP$_{25-35}$. These peptides form aggregates, including fibrils, in aqueous solution which, as described above, may be causative agents of increased neuronal cell calcium influx.

Our aim was to design or select antagonistic peptides, which we call decoy peptides (DPs), which (i) reduce aggregate formation by either blocking aggregation of β-amyloid peptides or, by incorporation into the nascent aggregate, make it inactive; (ii) are soluble in aqueous solutions but retain β-sheet forming potential associated with the multimer-forming amyloid peptide; and (iii) contain amino acids with charged side chains that can interfere with the interaction between β-amyloid aggregates and ligand-gated Ca$^{2+}$ channels. Decoy peptides are unlikely to interact with β-sheet regions of other biologically important proteins because, as noted above, such regions generally are buried in the tertiary structure of the protein and therefore inaccessible. Preferably, decoy peptides are resistant to proteolytic digestion, to increase usefulness of such peptides in therapeutic applications.

Previous reports of peptides active against aggregation of βAP (Soto et al., Biochem. Biophys. Res. Commun. 226:672–680, 1996; International Application Number PCT/US96/10220) described peptides which have a hydrophobic region but have a very low probability of the peptide to adopt a β-sheet conformation, and which have at least one β-sheet blocking amino acid within the hydrophobic region. These peptides were found to inhibit partially the βAP fibril formation and partially disaggregate preformed fibrils in vitro. The peptides were active only at high molar excess (10×) and were at most 50% effective. The peptides were not found to have effects on Ca$^{2+}$ influx or neurotoxicity.

We tested a library of random hexamer peptides prepared using six amino acids: glycine, alanine, isoleucine, valine, serine, and threonine. These amino acids were chosen in part because the β-sheet forming sequence in βAP$_{25-35}$ is G A I I (amino acids 5–8 of SEQ ID NO:10), and in part because we wanted some hydrophilic side chains present in the resulting random hexamer peptide as there are in βAP$_{25-35}$. All amino acids except glycine were D-amino acids to resist proteolysis. It will be apparent to one of ordinary skill in the art that other peptide libraries, both random and non-random (e.g. having amino acids selected to provide β sheet structure, or restricting the amino acids at certain positions of the peptides in the library), are useful according to the invention.

Other methods of constructing peptides which are resistant to proteolytic digestion are also possible, such as peptides including non-hydrolyzable peptide bonds, and peptides having end modifications such as an amide (e.g., CONH$_2$) at the C-terminus or a acetyl group at the N-terminus. Other methods of selecting decoy peptides are also possible, such as use of phage display libraries and synthesis of peptides based on existing decoy peptides or based on the β-amyloid peptides themselves. These options are covered in greater detail below.

It is believed that β-amyloid peptides are neurotoxic at least in part because they bind together to form multimers, or aggregates, which may even be fibrils of β-amyloid peptides linked together by binding of β-sheet structures of the β-amyloid peptides. Thus, compounds which prevent binding of β-amyloid peptides, which reduce the formation or size of the aggregates, such as fibrils, or which alter the tertiary structure and/or calcium influx stimulating properties of the aggregates can be useful for reducing the neurotoxicity of β-amyloid peptides. It has been discovered that a certain class of peptides, decoy peptides, is effective in reducing neurotoxic β-amyloid peptide aggregate formation.

The invention thus involves in one aspect the discovery of a mechanism of β-amyloid peptide aggregate cytotoxicity, which in turn enables intervening to interfere with that aggregate cytotoxicity by administration of compounds which antagonize the mechanism of cytotoxicity. A number of compounds which antagonize the mechanism of cytotoxicity have identified according to the methods of the invention. These compounds include organic molecules and inorganic molecules. In one aspect of the invention the compounds interfere with the ability of β-amyloid peptide to form neurotoxic aggregates, which aggregates cause unwanted cytotoxic calcium influx into cells. The compounds can affect neurotoxic aggregates by inhibiting binding of β-amyloid peptides to existing aggregates, by disrupting existing aggregates, by altering the structure of aggregates which incorporate the compound, by otherwise altering the structure of the aggregates (e.g. by capping) or by other mechanisms. Compounds useful in the invention also can interfere with unwanted calcium influx, e.g., by acting on the cell surface binding partner of the neurotoxic β-amyloid peptide aggregate, by reducing β-amyloid peptide aggregation, and the like. Examples of such compounds, discussed in greater detail below, include decoy peptides which inhibit or interfere with neurotoxic β-amyloid peptide aggregates and non-NMDA channel antagonists.

One particularly preferred compound useful according to the invention is the "decoy peptide". As discussed in greater detail below, using the methods of the invention we have identified several such decoy peptides. These are but examples of decoy peptides useful according to the invention, and were isolated using the methods of the invention described in the Examples. One such peptide was created by introducing an amino acid having a charged side chain into the middle of the sequence to favorably affect the function of the β-sheet structure that forms when the decoy peptide binds to its β-amyloid peptide binding partner. Another such peptide was created by introducing several proline residues into the peptide sequence. The foregoing changes to the peptides improved the function of the resultant peptides in the tests described below. Thus, it will be recognized by those of ordinary skill in the art, that other peptides will exist that function as described and can be easily isolated according to the methods of the invention. Likewise, various changes may be made including the addition of various side groups that do not affect the manner in which the decoy peptide binds to its binding partner, or which favorably affect the manner in which the decoy peptide binds to its binding partner. Such changes may involve adding or subtracting charge groups, substituting amino acids, adding lipophilic moieties that do not effect binding but that affect the overall charge characteristics of the molecule facilitating delivery across the blood-brain barrier, etc. For each such change, no more than routine experimentation is required to test whether the molecule functions according to the invention. One simply makes the desired change or selects the desired peptide and applies it in a fashion as described in detail in the examples. If the candidate molecule interferes with the ability of a β-amyloid peptide to form neurotoxic aggregates that cause an increase in calcium influx in neuronal cells, then the candidate a decoy peptide.

As used herein, a "decoy peptide" is one which binds to a β-amyloid peptide, such as βAP$_{1-40}$, βAP$_{1-42}$, or βAP$_{25-35}$, and thereby reduces the ability of β-amyloid peptide to form neurotoxic aggregates. The decoy peptides may inhibit neurotoxic aggregate formation by inhibiting formation of new aggregates, inhibiting binding of β-amyloid peptides to existing aggregates, disrupting existing aggregates, altering the structure of aggregates which incorporate the decoy peptides or by other mechanisms. While not being limited to any particular mechanism, it is believed that decoy peptides can inhibit β-amyloid peptide aggregate formation by presenting a β-sheet secondary structure which is compatible with and binds to existing β-amyloid peptide β-sheet structures, but which does not permit binding of additional β-amyloid peptides sufficient to form aggregates. Alternatively, decoy peptides can inhibit β-amyloid peptide aggregate formation and/or cytotoxicity by altering the structure of the aggregate sufficiently to reduce its cytotoxic effects.

Decoy peptides can be isolated by selecting peptides which bind to β-amyloid peptides, e.g. βAP$_{25-35}$, and reduce either neurotoxic β-amyloid peptide aggregate formation or existing neurotoxic β-amyloid peptide aggregates. β-amyloid peptide aggregate formation can be determined directly, e.g., by observation of the extent of β-amyloid peptide aggregate formation by microscopy, or indirectly, e.g., by determination of the effects of β-amyloid peptide aggregate formation, such as a change in neuronal cell calcium influx, as is described in the Examples below. Other methods for determining the extent or effects of β-amyloid peptide aggregate formation will be apparent to one of ordinary skill in the art.

Decoy peptides also can be isolated by selecting peptides which bind to β-amyloid peptides, e.g. βAP$_{25-35}$, and reduce unwanted calcium influx induced by β-amyloid peptide aggregates. Calcium influx can be measured as described herein, using indicator compounds which change a physical property (e.g., excitation/emission spectra) in response to a change in intracellular calcium concentration. Other methods for assaying changes in calcium influx useful in selecting decoy peptides or other compounds which oppose the effects of β-amyloid peptide aggregates on calcium influx will be known to one of ordinary skill in the art.

Still other methods for determining the effectiveness of a decoy peptide or other compound in inhibiting the neurotoxic effects of β-amyloid peptide aggregates can be used. For example, the effectiveness of decoy peptides against damage in rat brain slices caused by neurotoxic β-amyloid peptide aggregates can be determined. As another example, βAP fibrils can be injected into particular regions of rat brains to cause tissue damage which mimics the effects seen in Alzheimer's disease. Decoy peptides can be administered to determine the sparing effect of the decoy peptides. All of the foregoing methods are known in the art and can be employed using no more than routine experimentation.

Decoy peptides need not have both properties to be useful according to the invention. As is demonstrated below, it is possible to identify decoy peptides which do not inhibit β-amyloid peptide aggregation but do reduce β-amyloid-induced calcium influx, and vice versa. It is contemplated that decoy peptides having only one of the desirable properties identified herein are useful, although it is preferable that a decoy peptide have more than one of such properties, e.g., that the decoy peptide inhibits β-amyloid peptide aggregation and reduces β-amyloid peptide induced calcium influx.

Decoy peptides can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Decoy peptide candidates can be selected initially, for example, by screening libraries of peptides for those peptides which have the ability to disrupt β-amyloid peptide aggregate formation. Preferably, the library includes peptides which have β-sheet forming potential. β-sheet forming potential of peptides can be predicted from the amino acid sequence of the peptide by a known algorithm, such as the Chou-Fasman algorithm, which preferably applies equally to peptides containing D-amino acids. Peptide libraries may be structured so that peptides having β-sheet forming potential are preferentially included.

Decoy peptide candidates can be selected by contacting a peptide library with a β-amyloid peptide, such as $βAP_{25-35}$ or $βAP_{1-42}$, and determining the binding of candidate decoy peptides to the β-amyloid peptide. One such method for selecting decoy peptide candidates is provided in the Examples below, as well as libraries from which decoy peptides were isolated. Other methods, such as selecting peptides from a phage display library, are well-known in the art. Other libraries can be prepared from sets of amino acids with no more than routine experimentation.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to β-amyloid peptides such as $βAP_{25-35}$. This process can be repeated through several cycles of reselection of phage that bind to the β-amyloid peptides. Repeated rounds lead to enrichment of phage bearing particular sequences. DNA sequence analysis can be conducted to identify the sequences of the expressed polypeptides. The minimal linear portion of the sequence that binds to the β-amyloid peptides can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the β-amyloid peptides. Thus, the β-amyloid peptides, or a fragment thereof, can be used to screen peptide libraries, including phage display libraries, to identify and select peptide binding partners of the β-amyloid peptides such as $βAP_{25-35}$. Such molecules can be used, as described, for screening assays, for interfering directly with the functioning of β-amyloid peptides and for other purposes that will be apparent to those of ordinary skill in the art.

Selection of compounds which disrupt β-amyloid peptide aggregate formation is particularly contemplated. Methods for selecting such compounds include binding assays with which the art is familiar, as well as functional assays for determining the effects of such compounds on a biological response to aggregate formation, such as neuronal cell calcium influx. Methods for selecting compounds which disrupt β-amyloid peptide binding are provided in greater detail below.

Changes to the structure of a compound which disrupts β-amyloid peptide aggregate formation to form variants or analogs of such a compound can be made according to established principles in the art. Such changes can be made to increase the therapeutic efficacy of the compound, reduce side effects of the compound, increase or decrease the hydrophobicity or hydrophilicity, and the like. Changes to the structure include the addition of additional functional groups, such as for targeting the compound to a particular organ of a subject, and substitution of one or more portions of the compound. In general, substitutions involve conservative substitutions of particular moieties or subunits of the compound. For example, when preparing variants of a compound which is a peptide, one of ordinary skill in the art will recognize that conservative amino acid substitutions will be preferred, i.e., substitutions which retain a property of the original amino acid such as charge, β-sheet forming potential, etc. Examples of conservative substitutions of amino acids include substitutions made amongst amino acids within the following groups: (a) M, I , L, V; (b) F, Y, W; (c) K, R, H; (d) A, G; (e) S, T; (f) Q, N; and (g) E, D. Preferred substitutions include substitutions amongst β-branched amino acids. Of course, non-conservative substitutions can also be made to the peptide sequence of the decoy peptides, followed by testing the function of the substituted decoy peptide as described herein.

Preferably, decoy peptides are non-hydrolyzable. To provide such peptides, one may select decoy peptides from a library of non-hydrolyzable peptides, such as peptides containing one or more D-amino acids or peptides containing one or more non-hydrolyzable peptide bonds linking amino acids. Alternatively, one can select peptides which are optimal for disrupting β-amyloid peptide aggregation and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a decoy peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[$CH_2NH$]— reduced amide peptide bonds, -psi[$COCH_2$]— ketomethylene peptide bonds, -psi[$CH(CN)NH$]— (cyanomethylene)amino peptide bonds, -psi[$CH_2CH(OH)$]— hydroxyethylene peptide bonds, -psi[$CH_2O$]— peptide bonds, and -psi[$CH_2S$]— thiomethylene peptide bonds.

Decoy peptides preferably are short enough to be synthesized and isolated readily, yet long enough to effectively disrupt β-amyloid peptide aggregate formation. Preferred decoy peptides thus are between four and twenty amino acids in length, e.g., 4, 5, 6, 7, 8, 9, 10, 11, 12, 13, 14, 15, 16, 17, 18, 19, 20 amino acids. More preferably, decoy peptides are between five and ten amino acids in length. Those skilled in the art are well-versed in methods for preparing and isolating such peptides, such as synthetic chemistry or even recombinant biological methods.

Peptides useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (*Int. J. Pep. Protein Res.* 36:392–399, 1990) and Rivera—Baeza et al. (*Neuropeptides* 30:327–333, 1996) are also known to those of skill in the art.

Nonpeptide analogs of peptides, e.g., those which provide a stabilized structure or lessened biodegradation, are also contemplated. Peptide mimetic analogs can be prepared based on a selected decoy peptide by replacement of one or more residues by nonpeptide moieties. Preferably, the nonpeptide moieties permit the peptide to retain its natural confirmation, or stabilize a preferred, e.g., bioactive, confirmation. One example of methods for preparation of nonpeptide mimetic analogs from peptides is described in Nachman et al., *Regul Pept.* 57:359–370 (1995). Peptide as used herein embraces all of the foregoing.

Decoy peptides are useful in the treatment of conditions which are characterized by β-amyloid peptide aggregate formation. Decoy peptides also are useful for the selection of other compounds which interfere with neurotoxic β-amyloid peptide aggregate formation, e.g., by use of a decoy peptide in competition assays to select compounds which bind to β-amyloid peptides more avidly than the decoy peptide and which still interfere with neurotoxic β-amyloid peptide aggregate formation. Decoy peptides are also useful in the design of other compounds for disrupting β-amyloid peptide aggregate formation, such as small molecule inhibitors, based on the molecular structure of the decoy peptide. Thus, the decoy peptides can be used in vivo for the treatment of disease, as well as in vitro for the design and testing of compounds active in the disruption of β-amyloid peptide aggregate formation.

In some circumstances, it may be preferred to conjugate the decoy peptide to a compound which facilitates transport of the decoy peptide across the blood-brain barrier (BBB). As used herein, a compound which facilitates transport across the BBB is one which, when conjugated to the decoy peptide, facilitates the amount of decoy peptide delivered to the brain as compared with non-conjugated decoy peptide. The compound can induce transport across the BBB by any mechanism, including receptor-mediated transport, and diffusion. The decoy peptide can be conjugated to such compounds by well-known methods, including bifunctional linkers, formation of a fusion polypeptide, and formation of biotin/streptavidin or biotin/avidin complexes by attaching either biotin or streptavidin/avidin to the peptide and the complementary molecule to the BBB-transport facilitating compound.

Compounds which facilitate transport across the BBB include transferrin receptor binding antibodies (U.S. Pat. No. 5,527,527); certain lipoidal forms of dihydropyridine (see, e.g., U.S. Pat. No. 5,525,727); carrier peptides, such as cationized albumin or Met-enkephalin (and others disclosed in U.S. Pat. Nos. 5,442,043; 4,902,505; and 4,801,575); cationized antibodies (U.S. Pat. No. 5,004,697); and fatty acids such as docosahexanoic acid (DHA; U.S. Pat. No. 4,933,324).

For other uses of the decoy peptides, it may be preferred to administer the peptides in combination with a compound which increases transport of compounds across the blood-brain barrier (BBB). Such compounds, which need not be conjugated to a decoy peptide, increase the transport of the decoy peptide across the BBB into the brain. A compound which increases transport across the BBB is one, for example, which increases the permeability of the BBB, preferably transiently. Coadministration of a decoy peptide with such a compound permits the decoy peptide to cross a permeabilized BBB. Examples of such compounds include bradykinin and agonist derivatives (U.S. Pat. No. 5,112,596); and receptor-mediated permeabilizers such as A-7 (U.S. Pat. Nos. 5,268,164 and 5,506,206).

Compounds which reduce the ability of β-amyloid peptides to form aggregates which increase neuronal cell calcium influx, such as decoy peptides, can be administered to a subject to treat a condition characterized by unwanted β-amyloid peptide aggregates. Compounds such as decoy peptides are administered in an amount effective to reduce or inhibit formation of unwanted aggregates. By effective amount is meant an amount of a compound such as a decoy peptide which inhibits formation of new unwanted β-amyloid peptide aggregates, modifies the structure of new or existing unwanted aggregates so that the aggregates do not increase neuronal cell calcium influx, or destabilizes existing unwanted aggregates. β-amyloid peptide aggregates can include one or more of $\beta AP_{1-42}$, $\beta AP_{1-40}$ and $\beta AP_{25-35}$, as well as other components.

Conditions characterized by unwanted β-amyloid peptide aggregate formation include Alzheimer's Disease. It will be apparent to one of ordinary skill in the art that cytotoxicity of certain neuronal cells is involved in such conditions. For example, neuronal cells involved in Alzheimer's Disease include cells from hippocampal neurons, cortical layer 3 neurons, amygdala neurons, locus coeruleus neurons, and others known to be involved in memory formation and storage. It is envisioned that the compounds described herein, particularly decoy peptides, can be delivered to neuronal cells by site-specific means. Cell-type-specific delivery can be provided by conjugating a decoy peptide to a targeting molecule, e.g., one which selectively binds to the affected neuronal cells. Methodologies for targeting include conjugates, such as those described in U.S. Pat. No. 5,391,723 to Priest. Another example of a well-known targeting vehicle is liposomes. Liposomes are commercially available from Gibco BRL. Numerous methods are published for making targeted liposomes. Liposome delivery can be provided by encapsulating a decoy peptide in liposomes which include a cell-type-specific targeting molecule. Methods for targeted delivery of compounds to particular cell types are well-known to those of skill in the art.

Methods for reducing β-amyloid peptide induced neuronal cell calcium influx also are provided. The internal calcium concentration in neuronal cells can be affected by release of calcium from intracellular stores, influx of calcium from the extracellular milieu and possibly other sources. As described herein, β-amyloid peptides increase internal calcium concentrations by influencing the permeability of certain ligand-gated ion channels, the non-NMDA channels. Non-NMDA channels are ordinarily activated by a combination of two factors: (1) the presence of the excitatory amino acid neurotransmitter glutamate, and (2) a lack of magnesium ions at the cell surface following depolarization of the cell. Non-NMDA channels include subtypes for which AMPA ((RS)-2-amino-3-(3-hydroxy-5-methylisoxazol-4-yl)-propionate) and kainate are agonists.

The discovery of a calcium influx mechanism by which β-amyloid peptides induce neurotoxicity provides a basis for treating conditions characterized by β-amyloid peptide induced calcium influx. Thus, subjects can be treated by administering any compounds which reduce the β-amyloid peptide induced calcium influx. Such compounds can be inorganic or organic and can act on the β-amyloid peptide, the neurotoxic β-amyloid peptide aggregate or the cell surface binding partner of the neurotoxic β-amyloid peptide aggregate to interfere with unwanted calcium influx. Examples of such compounds include decoy peptides which inhibit or interfere with neurotoxic β-amyloid peptide aggregates, and non-NMDA channel antagonists. The compounds are administered in an effective amount, i.e., an amount which reduces the increased calcium influx. In neuronal cell types other than NT2-N cells differentiated with retinoic acid, β-amyloid peptides may induce neurotoxicity via calcium influx through other means, such as NMDA channels. It is contemplated, therefore, that antagonists of calcium channels other than non-NMDA channels can be administered to treat conditions characterized by β-amyloid peptide induced calcium influx.

Non-NMDA channel antagonists are well-known in the art. Such antagonists inhibit the calcium Influx by inhibiting the opening of a non-NMDA channel in response to its ligand, such as glutamate, AMPA, kainate or, according to the invention, neurotoxic β-amyloid peptide aggregates. Non-NMDA channel antagonists can act competitively or noncompetitively, and can block one or more subtypes of non-NMDA channels. Preferably, antagonists used are those which inhibit the function of only those channels opened by β-amyloid peptide aggregates. Useful non-NMDA antagonists include 6-cyano-7-nitroquinoxaline-2,3-dione (CNQX), 6,7-dinitroquinoxaline-2,3(1H, 4H)-dione (DNQX), 2,3-dihydroxy-nitro-7-sulfamoyl-benzo[f] quinoxaline (NBQX), 1-(4-chlorobenzoyl)piperazine-2,3-dicarboxylic acid (CBPD), 6,7-dichloro-2(1H)-oxoquinoline-3-phosphonic acid (24c), Evans blue, 2,3-dihydroxy-7-sulfamoyl-benzo[f]quinoxaline (BQX), derivatives of 4-oxo-1,4-dihydroquinoline-2-carboxylic acid at the 6-position, 2-amino-3-[3-(carboxymethoxy)-5-methylisoxazol-4-yl]propionic acid (AMOA), 2-amino-3-[2-(3-hydroxy-5-methylisoxazol-4-yl)-methyl-5-methyl-3-+++oxoisoxazolin-4-yl]propionic acid (AMNH), 1-(4-amino-phenyl)-4-methyl-7,8-methyl-endioxyl-5H-2,3-benzodiazepine (GYKI 52466), 6-(1H-imidazol-1-yl)-7-nitro- 2,3 (1H,4H)-quinoxalinedione hydrochloride (YM90K), 1-(4-aminophenyl)-3-methylcarbamyl-4-methyl-7,8-methylenedioxy-3,4-dihydro-5H-2,3-benzodiazepine (GYKI 53655), and (−)(3S,4aR,6R,8aR)-6-[2-(1 (2)H-tetrazole-5-yl)ethyl]-1,2,3,4,4a,5,6,7,8,8a-decahydroisoquinoline-3-carboxylic acid monohydrate (LY326325).

The invention further provides efficient methods of identifying pharmacological agents or lead compounds for agents useful in the treatment of conditions associated with β-amyloid peptide aggregation or conditions associated with increased neuronal cell calcium influx induced by the presence of β-amyloid peptide aggregates. Generally, the screening methods involve assaying for compounds which interfere with β-amyloid peptide aggregation or neuronal cell calcium influx through non-NMDA channels as regulated by β-amyloid peptide aggregates. Such methods are adaptable to automated, high throughput screening of compounds.

A wide variety of assays for pharmacological agents are provided, including, labeled in vitro peptide-peptide binding assays, $Ca^{2+}$ influx assays, etc. For example, peptide binding screens are used to rapidly examine the effect of candidate pharmacological agents on the binding of decoy peptides to β-amyloid peptide. The candidate pharmacological agents can be derived from, for example, combinatorial peptide libraries. Convenient reagents for such assays are known in the art. An exemplary cell-based assay involves contacting a neuronal cell with a mixture of β-amyloid peptide and a candidate pharmacological agent. A reduction in the induction of calcium influx by resulting β-amyloid peptide aggregates indicates that the candidate pharmacological agent disrupts β-amyloid peptide aggregate formation or reduces the sensitivity of calcium channels to β-amyloid peptide aggregates. Methods for determining changes in the intracellular calcium concentration are known in the art and are addressed elsewhere herein.

β-amyloid peptides used in the methods of the invention are added to an assay mixture as an isolated peptide. β-amyloid peptides can be produced recombinantly, or isolated from biological extracts, but preferably are synthesized in vitro. β-amyloid peptides encompass chimeric proteins comprising a fusion of a β-amyloid peptide with another polypeptide, e.g., a polypeptide capable of providing or enhancing protein-protein binding, or enhancing stability of the β-amyloid peptide under assay conditions. A polypeptide fused to a β-amyloid peptide or fragment may also provide means of readily detecting the fusion protein, e.g., by immunological recognition or by fluorescent labeling.

The assay mixture includes a β-amyloid peptide, such as $βAP_{1-42}$, $βAP_{1-40}$, and $βAP_{25-35}$, and can include a decoy peptide as described herein.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500. Candidate agents comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the $\beta$-amyloid peptide forms aggregates and specifically binds the cellular binding target and induces neuronal calcium influx, or specifically binds the decoy peptide. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the presence or absence of specific binding between the $\beta$-amyloid peptide and one or more binding partners is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as a calcium influx assay. The calcium influx resulting from $\beta$-amyloid peptide aggregation and binding to a target molecule typically alters a directly or indirectly detectable product, e.g., a calcium sensitive molecule such as fura-2-AM. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a $\beta$-amyloid peptide, decoy peptide or the candidate pharmacological agent.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

Thus the present invention includes automated drug screening assays for identifying compositions having the ability to inhibit ion influx in a cell induced by A$\beta$ aggregates, thus contributing to a detectable change in the cytoplasmic level of a predetermined ion in the cell, the cytoplasm of which cell contains an indicator which is sensitive to the ion. The method is carried out in an apparatus which is capable of delivering a reagent solution to a plurality of predetermined cell-containing compartments of a vessel and measuring the detectable change in the cytoplasmic level of the ion in the cells of the predetermined compartments, such as the apparatus and method described in U.S. Pat. No. 6,057,114. Exemplary methods include the following steps. First, a divided culture vessel is provided that has one or more compartments which contain viable cells which, when exposed to A$\beta$ aggregates, have a detectable change in the concentration of the predetermined ion in the cytoplasm. The cytoplasms of the cells include an amount of an ion-sensitive fluorescent indicator sufficient to detect a change, if any, in the concentration of the predetermined ion. A$\beta$ aggregates are added to the cells to induce calcium influx and/or depolarization. Next, one or more predetermined cell-containing compartments are aligned with a predetermined position (e.g., aligned with a fluid outlet of an automatic pipette) and an aliquot of a solution containing a compound or mixture of compounds being tested for its ability to modulate A$\beta$ fibril-induced calcium influx and/or depolarization is delivered to the predetermined compartment(s) with an automatic pipette. Finally, fluorescence emitted by the ion-sensitive indicator in response to an excitation wavelength is measured for a predetermined amount of time, preferably by aligning said cell-containing compartment with a fluorescence detector. Preferably, fluorescence also measured prior to adding A$\beta$ aggregates to the cells and/or prior to adding the compound to the wells, to establish e.g., background and/or baseline values for fluorescence.

In accordance with the various assays of the present invention, cells are employed which have ion channels and/or receptors, the activation of which by aggregated Aβ peptides (i.e., Aβ aggregates or fibrils) results in a change in the level of a cation or anion in the cytoplasm. The cytoplasm of the cells employed are loaded with a fluorescent indicator which is sufficiently sensitive to said ion. By the phrase "sufficiently sensitive fluorescent indicator" is meant a fluorescent compound which, in the presence of, and over a range of physiological concentrations of, a particular ion, is capable of producing distinguishable levels of fluorescence intensity. Preferably, a fluorescent indicator should be able to produce detectably different intensities of fluorescence in response to relatively small changes in ion concentration. The relative intensities of fluorescence when the receptors or ion channels have not been activated, as compared to when the receptors or ion channels have been activated, preferably differ by at least about 50% or more, more preferably by at least about 100–200%.

Any cell which is capable, upon exposure to Aβ aggregates, of directly increasing the intracellular concentration of calcium, such as by permitting calcium influx through calcium channels or ion pores formed in accordance with the ionophore properties of Aβ aggregates, or by causing release of calcium from intracellular stores, may be used in the assay. Preferably neuronal cell lines or cultured neurons are used. Such cells include, but are not limited to, the hNT neuronal cells used in the Examples.

Activation of cellular receptors and/or ion channels (e.g., AMPA/kainate-type channels) by incubation with Aβ aggregates and/or ionophore formation by Aβ aggregates, may result in a transient increase in the level of intracellular calcium (and/or other ions). The initial increase in calcium may be detected as a rapid increase in fluorescence (e.g., within one to two seconds) after the addition of the Aβ aggregates. As shown herein, calcium influx is generally short-lived, but depolarization is longer lasting. Fluorescence levels in the cytoplasm resulting from calcium influx typically increase to a peak value and then typically decline as excess calcium ions are removed by normal cellular mechanisms. Fluorescence due to depolarization after Aβ fibril exposure rapidly increases to a plateau value, and remains at this plateau. The speed at which the fluorescence can be analyzed is important for analysis of the kinetics of the reaction, if it is desired to measure kinetics.

The cells used in the assays of the invention are loaded with a fluorescent indicator which is sufficiently sensitive so as to produce detectable changes in fluorescence intensity in response to changes in the concentration of the ions in the cytoplasm. It is particularly preferred to use a fluorescent indicator which has such sensitivity in the presence of calcium ions, although indicators sensitive to other ions such as sodium ions, potassium ions, chloride ions, and the like may be employed depending on the type of ion flux induced by the Aβ aggregates, as will be understood by the person of ordinary skill in the art. Among the fluorescent indicators which may be employed are the following compounds commercially available from, e.g., Molecular Probes, Inc., Eugene Oreg.: DiBAC$_4$(3) (B-438), Quin-2 (AM Q-1288), Fura-2 (AM F-1225), Indo-1 (AM I-1226), Fura-3 (AM F-1228), Fluo-3 (AM F-1241), Rhod-2, (AM R-1244), BAPTA (AM B-1205), 5,5'-dimethyl BAPTA (AM D-1207), 4,4'-difluoro BAPTA (AM D-1216), 5,5'-difluoro BAPTA (AM D-1209), 5,5'-dibromo BAPTA (AM D-1213), Calcium Green (C-3011), Calcium Orange (C-3014), Calcium Crimson (C-3017), Fura-5 (F-3023), Fura-Red (F-3020), SBFI (S-1262), PBFI (P-1265), Mag-Fura-2 (AM M-1291), Mag-Indo-1 (AM M-1294), Mag-Quin-2 (AM M-1299), Mag-Quin-1 (AM M-1297), SPQ (M-440), and SPA (S460).

It is contemplated that each of the individual wells contain the same cell type so that multiple compounds (obtained from different reagent sources in the apparatus or contained within different wells) can be screened and compared for modulating activity with respect to Aβ fibril-induced calcium influx and/or depolarization.

In another of its aspects the invention entails automated antagonist assays. Antagonist assays, including drug screening assays, may be carried out by incubating the cells (e.g., neurons) with Aβ aggregates to induce calcium influx and/or depolarization, in the presence and absence of one or more compounds added to the solution bathing the cells in the respective wells of the microtiter plate for an amount of time sufficient for the compound(s) to modulate calcium influx and/or depolarization, and measuring the level of fluorescence in the cells as compared to the level of fluorescence in either the same cell, or substantially identical cell, in the absence of the Aβ aggregates.

As will be understood by the person of ordinary skill in the art, compounds exhibiting agonist or antagonist activity in an assay of calcium influx or depolarization will either increase or decrease intracellular ion levels (agonist) or inhibit (antagonist) an increase or decrease in the intracellular concentration of ions after incubation of cells with Aβ aggregates. It is desirable to measure the amount of agonist or antagonist activity in a linear range of the assay system, such that small but significant increases or decreases in fluorescence relative to control well (e.g., devoid of the test compound) may be observed. It is well within the skill of the art to determine a volume and concentration of a reagent solution which causes a suitable activation response in cells so that modulation of the calcium influx and/or depolarization may be reliably detected.

At a suitable time after addition of the Aβ aggregates to initiate calcium influx and/or depolarization, the plate is moved, if necessary, so that the cell-containing assay well is positioned for measurement of fluorescence emission. Because a change in the fluorescence signal may begin within the first few seconds after addition of test compounds, it is desirable to align the assay well with the fluorescence reading device as quickly as possible, with times of about two seconds or less being desirable. In preferred embodiments of the invention, where the apparatus is configured for detection through the bottom of the well(s) and compounds are added from above the well(s), fluorescence readings may be taken substantially continuously, since the plate does not need to be moved for addition of reagent. The well and fluorescence-reading device should remain aligned for a predetermined period of time suitable to measure and record the change in intracellular ion, e.g., calcium, concentration. In preferred embodiments of the invention the fluorescence after activation is read and recorded until the fluorescence change is maximal and then begins to reduce. An empirically determined time period may be chosen which covers the transient rise and fall (or fall and rise) of intracellular ion levels in response to addition of the compound. Wheb the apparatus is configured to detect fluorescence from above the plate, it is preferred that the bottom of the wells are colored black to reduce the background fluorescence and thereby decreases the noise level in the fluorescence reader.

After finishing reading and recording the fluorescence in one well, the just described apparatus steps are repeated with the next well(s) in the series so as to measure pre-reagent fluorescence, add reagent and measure and record the transient change, if any, in fluorescence. The apparatus of the present invention is programmable to begin the steps of an assay sequence in a predetermined first well (or row or column of wells) and proceed sequentially down the columns and across the rows of the plate in a predetermined route through well number n.

In assays of cells treated with Aβ aggregates to cause an increase in intracellular calcium ion concentration and/or depolarization, it is preferred that the fluorescence data from replicate wells of cells treated with the same compound are collected and recorded (e.g., stored in the memory of a computer) for calculation of fluorescence and/or intracellular calcium ion concentration.

In assays of compounds that inhibit calcium influx and/or depolarization, the results can be expressed as a percentage of the maximal response caused by Aβ aggregates (e.g., Aβ1-42 aggr.). The maximal fluorescence increase caused by Aβ aggregates is defined as being 100% response. For compounds effective for reducing calcium influx and/or depolarization induced by Aβ aggregates, the maximal fluorescence recorded after addition of a compound to wells containing Aβ aggregates is detectably lower than the fluorescence recorded in the presence of only Aβ aggregates.

The fluorescence indicator-based assays of the present invention are thus useful for rapidly screening compounds to identify those that modulate calcium influx and/or depolarization that ultimately results in an altered concentration of ions in the cytoplasm of a cell. For example, the assays can be used to test functional ligand interactions with Aβ aggregates or ligand competition with decoy peptide binding of Aβ aggregates.

Automation of the fluorescent dye-based assays of the invention can be performed as described in U.S. Pat. No. 6,057,114. Automation can provide increased efficiency in conducting the assays and increased reliability of the results by permitting multiple measurements over time, thus also facilitating determination of the kinetics of the calcium influx or depolarization effects.

For example, to accomplish rapid compound addition and rapid reading of the fluorescence response, the fluorometer can be modified by fitting an automatic pipetter and developing a software program to accomplish precise computer control over both the fluorometer and the automatic pipetter. By integrating the combination of the fluorometer and the automatic pipetter and using a microcomputer to control the commands to the fluorometer and automatic pipetter, the delay time between reagent addition and fluorescence reading can be significantly reduced. Moreover, both greater reproducibility and higher signal-to-noise ratios can be achieved as compared to manual addition of reagent because the computer repeats the process precisely time after time. Moreover, this arrangement permits a plurality of assays to be conducted concurrently without operator intervention. Thus, with automatic delivery of reagent followed by multiple fluorescence measurements, reliability of the fluorescent dye-based assays as well as the number of assays that can be performed per day are advantageously increased.

The invention provides compounds which bind to a β-amyloid peptide and reduces the ability of the β-amyloid peptide to form neurotoxic aggregates which increase calcium influx into neuronal cells and compounds which disrupt increased neuronal cell calcium influx induced by the presence of β-amyloid peptide aggregates, methods of identifying and making such agents, and their use in diagnosis, therapy and pharmaceutical development. For example, β-amyloid peptide-specific pharmacological agents are useful in a variety of diagnostic and therapeutic applications, especially where disease or disease prognosis is associated with improper utilization of a pathway involving β-amyloid peptide, e.g., β-amyloid peptide aggregation, neuronal cell calcium influx associated with neurotoxic β-amyloid peptide aggregates, etc. Novel β-amyloid peptide-specific binding agents include decoy peptides and other natural binding agents identified with the above-described assays, and non-natural intracellular binding agents identified in screens of chemical libraries and the like.

Decoy peptides or other compounds which antagonize the formation of neurotoxic β-amyloid peptide aggregates may be administered as part of a pharmaceutical composition. Such a pharmaceutical composition may include the peptides in combination with any standard physiologically and/or pharmaceutically acceptable carriers which are known in the art. The compositions should be sterile and contain a therapeutically effective amount of the decoy peptides or other therapeutic compound in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which desirably influence the existence or formation of aggregates of β-amyloid peptides that induce calcium influx in neuronal cells, and/or desirably influence the cytotoxic effects of such aggregates. Generally, a therapeutically effective amount will vary with the subject's age, and condition, as well as the nature and extent of the disease in the subject, all of which can be determined by one of ordinary skill in the art. The dosage may be adjusted by the individual physician, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days.

The therapeutics of the invention can be administered by any conventional route, including injection or by gradual infusion over time. The administration may, for example, be oral, intravenous, intracranial, intraperitoneal, intramuscular, intracavity, intrarespiratory, subcutaneous, or transdermal. The route of administration will depend on the composition of a particular therapeutic preparation of the invention.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating conditions characterized by aggregates of β-amyloid peptides by placing the implant near portions of the brain affected by such aggregates, thereby effecting localized, high doses of the compounds of the invention.

Depending upon the nature of the reactive groups in a decoy peptide and a targeting agent or blood-brain barrier transport compound, a conjugate can be formed by simultaneously or sequentially allowing the functional groups of the above-described components to react with one another. For example, the transport-mediating compound can be prepared with a sulfhydryl group at, e.g., the carboxyl terminus, which then is coupled to a derivatizing agent to form a carrier molecule. Next, the carrier molecule is attached via its sulfhydryl group, to the decoy peptide. Many other possible linkages are known to those of skill in the art.

Conjugates of a decoy peptide and a targeting agent or BBB transport-facilitating compound are formed by allowing the functional groups of the agent or compound and the peptide to form a covalent linkage using coupling chemistries known to those of ordinary skill in the art. Numerous art-recognized methods for forming a covalent linkage can be used. See, e.g., March, J., *Advanced Organic Chemistry*, 4th Ed., New York, N.Y., Wiley and Sons, 1985, pp. 326–1120.

For decoy peptides which exhibit reduced activity in a conjugated form, the covalent bond between the decoy peptides and the BBB transport-mediating compound is selected to be sufficiently labile (e.g., to enzymatic cleavage by an enzyme present in the brain) so that it is cleaved following transport of the decoy peptides across the BBB, thereby releasing the free decoy peptides to the brain. Art-recognized biologically labile covalent linkages, e.g., imino bonds, and "active" esters can be used to form prodrugs where the covalently coupled decoy peptides is found to exhibit reduced activity in comparison to the activity of the decoy peptides alone. Exemplary labile linkages are described in U.S. Pat. No. 5,108,921, issued to Low et al.

If the decoy peptides does not have a free amino-or carboxyl-terminal functional group that can participate in a coupling reaction, such a group can be introduced, e.g., by introducing a cysteine (containing a reactive thiol group) into the peptide by synthesis or site directed mutagenesis. Disulfide linkages can be formed between thiol groups in, for example, the decoy peptide and the BBB transport-mediating compound. Alternatively, covalent linkages can be formed using bifunctional crosslinking agents, such as bismaleimidohexane (which contains thiol-reactive maleimide groups and which forms covalent bonds with free thiols). See also the Pierce Co. Immunotechnology Catalogue and Handbook Vol. 1 (Pierce, Rockford, Ill.) for a list of exemplary homo-and hetero-bifunctional crosslinking agents, thiol-containing amines and other molecules with reactive groups.

Other methods for covalently coupling the transport-mediating peptide to the derivatizing agent and/or to the extracellular agent include, for example, methods involving glutaraldehyde (Riechlin, *Methods Enzymol.* 70:159–165, 1980); N-ethyl-N'-(3-dimethylaminopropyl)-carbodiimide (Goodfriend et al., *Science* 144:1344–1346, 1964); and a mixture of N-ethyl-N'-(3-dimethylaminopropyl)-carbodiimide and a succinylated carrier (Klapper and Klotz, *Methods Enzymol.* 25:531–536, 1972). In general, the conjugated decoy peptides of the invention can be prepared by using well-known methods for forming amide, ester or imino bonds between acid, aldehyde, hydroxy, amino, or hydrazo groups on the respective conjugated decoy peptide components. As would be apparent to one of ordinary skill in the art, reactive functional groups that are present in the amino acid side chains of the decoy peptide (and possibly in the BBB transport-mediating compound) preferably are protected, to minimize unwanted side reactions prior to coupling the peptide to the derivatizing agent and/or to the extracellular agent. As used herein, "protecting group" refers to a molecule which is bound to a functional group and which may be selectively removed therefrom to expose the functional group in a reactive form. Preferably, the protecting groups are reversibly attached to the functional groups and can be removed therefrom using, for example, chemical or other cleavage methods. Thus, for example, the peptides of the invention can be synthesized using commercially available side-chain-blocked amino acids (e.g., FMOC-derivatized amino acids from Advanced Chemtech.Inc., Louisville, Ky.). Alternatively, the peptide side chains can be reacted with protecting groups after peptide synthesis, but prior to the covalent coupling reaction. In this manner, conjugated decoy peptides of the invention can be prepared in which the amino acid side chains do not participate to any significant extent in the coupling reaction of the peptide to the BBB transport-mediating compound or cell-type-specific targeting agent.

EXAMPLES

Example 1

Preparation of $\beta AP_{25-35}$ and $\beta AP_{1-42}$ $\beta AP_{25-35}$ was synthesized using standard peptide chemistry by the BioPolymers Laboratory at the Massachusetts Institute of Technology and purified by HPLC. $\beta AP_{1-42}$ was purchased from Quality Control Biochemicals Stock solutions of $\beta AP_{25-35}$ were prepared in DMSO at 20–100 mM. In solution, $\beta AP_{25-35}$ tended to aggregate during frozen storage as well as at room temperature, due to the presence of seed aggregates. Stock solutions in DMSO were filtered immediately by spin filtering with Ultrafree-MC filters of low-binding regenerated cellulose with a molecular cut-off at 30,000 MW (Cat. No. UFC3LTK00; Millipore Corporation, Bedford, Mass.). Without immediate filtration, the DMSO stock solution is unstable, even at −40□C, due to the presence of nuclei of aggregation that lead to very rapid aggregation. Concentration of the filtrate was determined by amino acid analysis. Aliquots of the filtered stock solutions can be stored for several weeks at −40□C. When using the stock solution to treat cells, the DMSO stock solution of the peptide is diluted into aqueous Tyrode's solution (Stratagene, La Jolla, Calif.), with or without calcium, shortly before use. Final DMSO concentrations preferably are kept below 0.1%. The absence of seed aggregates removed by the filtration process described above delays aggregation of the $\beta AP_{25-35}$.

Example 2

$\beta AP_{25-35}$ Increases Internal Calcium Concentration

We determined the internal calcium concentration, $[Ca^{2+}]_{int}$, of hNT cells in the absence or in the presence of $\beta AP_{25-35}$ or $\beta AP_{1-42}$.

hNT cells (Stratagene, La Jolla, Calif.) are derived from the human teratocarcinoma cell line (NT2-N) differentiated with retinoic acid. These cells have a neuronal morphology and possess NMDA and non-NMDA ligand-gated channels and voltage-gated calcium channels. hNT cells were plated 4–20 days before use on poly-D-lysine-coated acid washed glass coverslips in Stratagene's conditioned medium and growth medium. Only single phase-bright cells, connected by extensive neurite extensions, were used. (Many hNT cells were clumped together without sprouting neurites). For estimation of internal calcium concentration the coverslips were placed in a coverslip holder (Medical Systems Corp.).

hNT cells were loaded with fura-2-AM, dissolved in Pluronic acid F127 (20% in DMSO) as described by the supplier (Molecular Probes, Eugene, Oreg.). Fura-2-AM loading was at room temperature with 3 $\mu$M fura-2-AM in Tyrode's solution with 2 mM calcium (Tyr2Ca). Cells were subsequently washed and allowed to recover at 37□C for 30 minutes either in Tyr2Ca solution alone or with the low concentration of DMSO (<<1%) that resulted from the dilution of DMSO stock solutions of the peptides. Loaded cells were examined at room temperature in 400 $\mu$L of control Tyr2Ca, containing the appropriate concentration of DMSO. It took 10–20 minutes to measure $[Ca^{2+}]_{int}$, in approximately 10 cells under a particular condition. The solution covering the cells next was exchanged carefully for 400 $\mu$L of the test solution. All solutions were in Tyr2Ca. Using a Nikon Diaphot inverted microscope with a Fluor-40 objective, $[Ca^{2+}]_{int}$, was determined for these cells with the PTI Ratiometric photomultiplier technology (RM-M System and Felix Software). The emission fluorescence at 510 mM was measured over an excitation range of 320–400 nM. The ratio of 510 nM emissions at 340 nM and at 380 nM was used to calculate $[Ca^{2+}]_{int}$ from a standard calcium concentration curve made with fura-2, sodium salt, and standard calcium solutions supplied by Molecular Probes (Cat. No. C3B009).

Alternatively, the internal calcium concentration can be determined by continuous monitoring of fura-2 fluorescence at 510 nm using the same equipment as above. Fura-2 is excited alternately at 340 nm and 380 nm and the emission at 510 nm is recorded. Aggregated β-amyloid peptide produces a sharp peak of internal calcium concentration followed by an exponential decay to a plateau level of internal calcium concentration. The continuous measurement of fura-2 fluorescence permits a determination of the effect of decoy peptides on the peak internal calcium concentration, the plateau internal calcium concentration, or both.

Cell cultures that were exposed to $\beta AP_{25-35}$, and that in consequence had an elevated $[Ca^{2+}]_{int}$, tended to detach from the glass coverslip. Thus, the cells that remained attached tended to be those in which the first treatment evoked only a very low rise in $[Ca^{2+}]_{int}$, leading to a very biased population of cells for subsequent experiments. At the same time, the overall morphology of the cell and the extent of the neurite networks did not change greatly, if at all. Accordingly, all experiments exposed the neuronal cells to just one test solution.

FIG. 1 shows the effect on the internal calcium concentration of the addition of an unfiltered suspension of $\beta AP_{25-35}$ (panels A, B) or $\beta AP_{1-42}$ (panels C, D) in Tyr2Ca applied to hNT cells. Panel A shows that hNT cells in Tyr2Ca medium had an average $[Ca^{2+}]_{int}$ of 80 nM (column 1). Exposure to unfiltered $\beta AP_{25-35}$ at 20 $\mu$M increased $[Ca^{2+}]_{int}$ to approximately 200 nM (column 2), decreasing only slightly after 30 min (column 3). The final concentration of DMSO was 0.04% in both conditions. Each column represents the mean $[Ca^{2+}]_{int}$ of 8 cells±± the standard deviation of the mean the significance of the mean from the means of the controls is expressed as **P<0.0001. Panel B shows that hNT cells in Tyr2Ca medium had an average $[Ca^{2+}]_{int}$ of 50 nM (column 1) in this experiment. Exposure to unfiltered aggregated $\beta AP_{1-42}$ (37□C, 24 hr) at 20 $\mu$M increased $[Ca^{2+}]_{int}$ to approximately 94 nM (column 2); **P<0.0001. Panels C and D shows a display of the $[Ca^{2+}]_{int}$ in individual cells in panels A and B, respectively. Open squares, control; upward triangles, immediated effect of the addition of $\beta AP_{25-35}$ or $\beta AP_{1-42}$; inverted triangles, the effect after 30 min.

Table 1 shows the changes in $[Ca^{2+}]_{int}$ in hNT cells in response to different concentrations of $\beta AP_{25-35}$. An unfiltered suspension of $\beta AP_{25-35}$ in Tyr2Ca was added to hNT cells as described above, at the concentrations shown in Table 1. $[Ca^{2+}]_{int}$ is expressed as percent of control, with means±standard deviation indicated. There was a trend of increasing cytosolic calcium with increasing peptide concentration. This increase was stable for as long as 1 hour, with little if any desensitization. The effect was not readily reversible when the peptide was removed from the external medium. It was observed frequently that hNT cells treated with a peptide detached if a second change of external medium was attempted, but there was no obvious change in the well-differentiated morphology of the treated cells before lift-off.

TABLE 1

Effect of Different Concentrations of $\beta AP_{25-35}$ on $[Ca^{2+}]_{int}$ in hNT cells

| $[\beta AP_{25-35}]$ | % increase in $[Ca^{2+}]_{int}$ | P[a] | n[b] |
|---|---|---|---|
| 10 $\mu$M | 170 ± 85 | <0.05 | 9 |
| 20 $\mu$M | 286 ± 179 | <10⁻⁹ | 70 |
| 50 $\mu$M | 343 ± 245 | <10⁻⁵ | 22 |
| 112–114 $\mu$M | 366 ± 260 | <10⁻⁵ | 16 |
| 130 $\mu$M | 623 ± 555 | <0.05 | 11 |
| 172 $\mu$M | 367 ± 108 | <10⁻⁶ | 8 |
| 334 $\mu$M | 508 ± 561 | <0.05 | 9 |

[a]Difference from Tyrode's/2 mM Ca control; by paired Student's t-test.
[b]Number of responding cells 145/163 = 89%.

These experiments also indicated that the control levels of $[Ca^{2+}]_{int}$ were somewhat variable, perhaps dependent upon the length of time the hNT cells had been in culture. Starting with a supply of already differentiated hNT cells from Stratagene, cells could be maintained in culture up to 3 weeks. The control level of $[Ca^{2+}]_{int}$ in this series of experiments were between 43–85 nM. The effect of externally adding $\beta AP_{25-35}$ to the cell culture was recorded during the first 15 minutes of exposure to the peptides. There was relatively little desensitization or reversal of $[Ca^{2+}]_{int}$ during the next 30–45 minutes. Because 10–12 cells per dish were observed, any individual cell may have been measured after a period as short as 1.5 minutes or as long as 20 minutes after addition of peptide.

These data are derived from experiments in which the treatment immediately followed the control Tyrode's solution. Within each experiment involving 6–12 cells on one coverslip, there was considerable variability from cell to cell in the magnitude of the effect on cytosolic calcium concentrations, as is expressed by the standard deviation of the mean given herein.

Similar experiments in which the concentration of the $\beta AP_{1-42}$ peptide was increased also demonstrated a strong concentration dependence for calcium influx.

In other experiments, the external solution was changed to contain 20 mM EGTA in addition to $\beta AP_{25-35}$ peptide. The presence of EGTA decreased internal calcium to control levels, presumably by chelating external calcium and thereby drawing out internal calcium.

Figure 2:
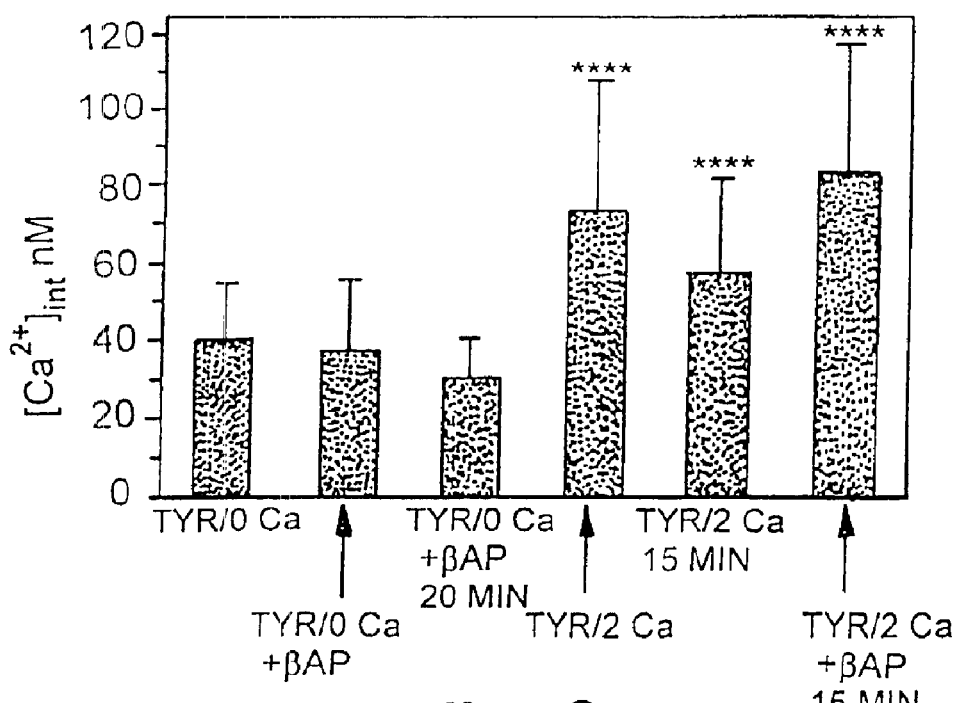
FIG. 2 is a bar graph which shows that increased internal $Ca^{2+}$ is derived from the external medium only.

To determine the origin of the increased internal calcium concentration, cells were exposed to concentrations of the $\beta AP_{25-35}$ peptide as above, in an external Tyrode's solution that had no calcium (FIG. 2). The same cells were exposed to Tyrode's/0 mM Ca plus 50 $\mu$M $\beta AP_{25-35}$ (from unfiltered stock), Tyrode's/2 mM Ca without $\beta AP_{25-35}$ and Tyrode's/2 mM Ca plus 50 $\mu$M $\beta AP_{25-35}$. Some measurements were repeated after 15 or 20 minutes, as indicated. The mean control value for cells in Tyrode's/0 mM Ca was 44 nM. The results are shown ±S.D. The significance of the means of the last 3 columns from the initial Tyrode's/0 mM Ca condition was calculated by the paired Student's t-test: *P<0.001; ** P<0.0001. As shown in FIG. 2, there was no increase in internal calcium, even after 15 minutes of exposure to peptide. Restoring external calcium to 2 mM, even without adding extra peptide, at once caused a substantial increase in internal calcium concentration to almost 200% of control levels. This increase was increased slightly by further addition of external peptide. Therefore, it was concluded that the increased $[Ca^{2+}]_{int}$ is derived from the external medium only. These experiments also deomnstrate that the effect of $\beta AP_{25-35}$ was not reversible, because replacement of the peptide by Tyrode's/2 mM Ca caused immediate influx of calcium.

Figure 3:
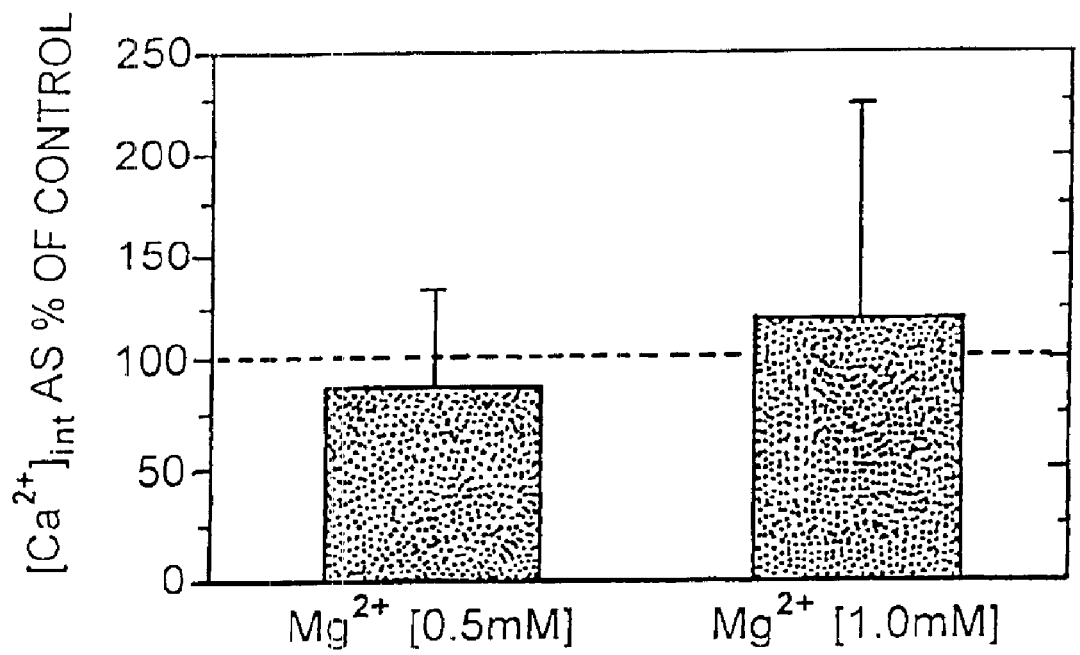
FIG. 3 is a bar graph which shows that $Mg^{2+}$ blocks the influx of $Ca^{2+}$ caused by $\beta AP_{25-35}$.

To determine if magnesium had any affect on the influx of calcium, cells were treated as described above, with the addition of magnesium concentrations as shown in FIG. 3. Each column represents $[Ca^{2+}]_{int}$±S.D. for separate experiments in which hNT cels were first exposed to the control solution of Tyrode's/2 mM Ca. The external solution was then replaced by a test solution containing $\beta AP25$-$35$ at about 20 $\mu$M and also MgCl$_2$ at either 0.5 mM (n=18) or 1 mM (n=5) in Tyrode's/2 mM Ca. The experiments depicted in FIG. 3 showed that 0.5 mM or 1 mM magnesium chloride. totally blocked the peptide-induced influx of calcium.

Figure 4:
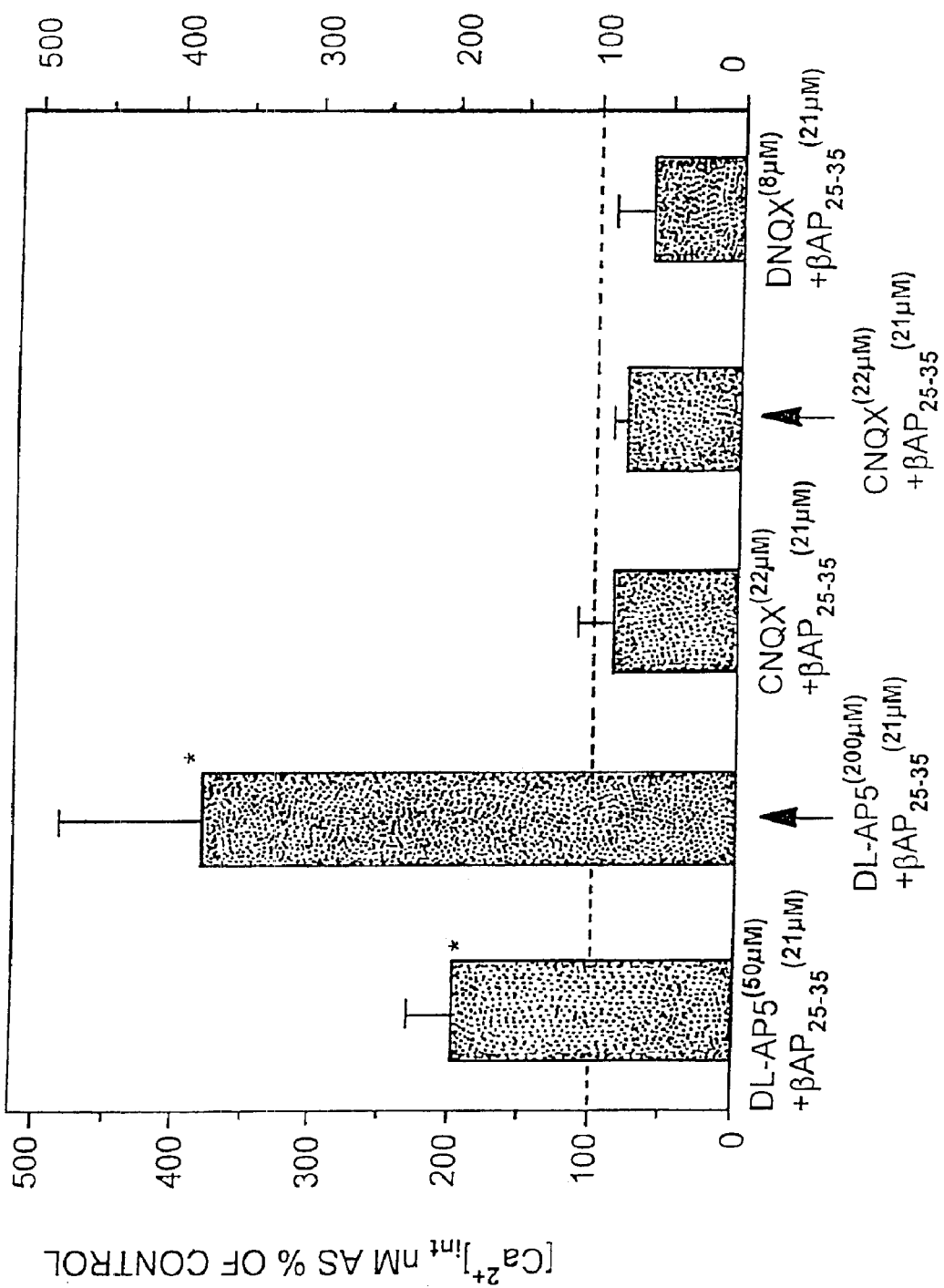
FIG. 4 is a bar graph which shows the response of $\beta AP_{25-35}$-induced $Ca^{2+}$ influx to NMDA and non-NMDA channel antagonists.

It was next determined whether antagonists of NMDA or non-NMDA ligand-gated channels had an effect on the increase of internal calcium concentrations in response to incubation with $\beta AP_{25-35}$. The results of these experiments are shown in FIG. 4. hNT cells were first exposed to the control solution of Tyrode's/2 mM Ca. The external solution was then replaced by a test solution containing $\beta AP_{25-35}$ (21 $\mu$M) and also a NMDA blocker, DL-AP5 (DL-2-amino-5-phosphonovaleric acid, (Sigma, St. Louis, Mo.)) at 50 $\mu$M or 200 $\mu$M, or the non-NMDA antagonists, CNQX (6-cyano-7-nitroquinoxaline-2,3-dione, (Sigma, St. Louis, Mo.)) at 22 $\mu$M, and DNQX (6,7-dinitroquinoxaline-2,3(1H, 4H)-dione) at 8 $\mu$M, as indicated. The dotted line indicates the control level of $[Ca^{2+}]_{int}$. The results are shown ±S.D. The addition of DL-AP5 at 50 $\mu$M or 200 $\mu$M failed to prevent $\beta AP_{25-35}$-induced calcium influx, as indicated by a significant difference in $[Ca^{2+}]_{int}$ as conpared to control. In contrast, addition of CNQX at 22 $\mu$M or DNQX at 8 $\mu$M completely prevented $\beta AP_{25-35}$-induced calcium influx. The fourth bar from the left represents data from a single experiment in which 4 cells had been first exposed to 21 $\mu$M $\beta AP_{25-35}$ and showed $[Ca^{2+}]_{int}$ at 270% of control. The value of $[Ca^{2+}]_{int}$ fell to control levels when the external solution was changed to contain, in addition to $\beta AP_{25-35}$, CNQX at 22 $\mu$M. Therefore, the NMDA channel antagonist, DL-AP5, fails to prevent the peptide-induced influx of calcium. However, CNQX and DNQX, antagonists of non-NMDA channels, prevents $\beta AP_{25-35}$-induced calcium influx when added before or after the addition of the $\beta$-amyloid peptide. Thus, non-NMDA channels mediate calcium influx in response to exposure of hNT cells to $\beta AP_{25-35}$.

Example 3

Preparation of a Decoy Peptide Combinatorial Library

A combinatorial library of potential decoy peptides was prepared by synthesizing a library of random hexamer peptides covalently linked to microspheres. The random library was constructed from D-amino acids so that any peptides isolated from the library would be useful as therapeutics by resisting proteolysis when administered to a subject. We chose, therefore, to chemically synthesize the peptide library rather than using the phage display method well known in the art.

The peptide library was prepared according to the method described by Lam (*Nature* 354:82–84, 1991) 5 D-amino acids (Ala, Ile, Val, Ser, Thr) and Gly were used to prepare a library representing 46,500 individual peptide sequences of 6 amino acids each. The peptides were attached by the C-terminus to a polystyrene bead, via a linker of 3 Gly residues. This was done in order to facilitate interaction between a member of the peptide library, covalently attached to a bead, and a fluorescently tagged $\beta AP_{25-35}$ peptide. The particular amino acids chosen were chosen on the basis of the $\beta$-sheet forming portion of the $\beta AP_{25-35}$ peptide. It was reasoned that a peptide containing a $\beta$-sheet forming region would be able to bind to and disrupt formation of aggregates of $\beta AP_{25-35}$.

The following schema was used to obtain a library of random hexapeptides covalently attached to polystyrene beads, so that each bead contained a unique sequence. The starting beads were NH$_2$-GGG-(polystyrene).

Step One. The pool of beads was divided into 6 aliquots. The first aliquot was reacted with D-Ala, the second with D-Val, the third with D-Ile, and so forth using D-Ser, D-Thr or D-Gly.

Step Two. The six pools were combined and then divided into six equal aliquots. The first was reacted with D-Ala, the second was reacted with D-Val, the third with D-Ile, and so forth using D-Ser, D-Thr, or Gly.

Steps Three, Four, Five and Six were performed in the same manner as Steps One and Two.

The final combination gave a library of 46,500 individual sequences randomly composed of the 6 amino acids. The first library of decoy peptides contained no amino acids having charged side chains. The library was stored dry at −40□C. Peptides were synthesized either with a —COOH terminus or with an amide terminus (—CONH$_2$). It was later shown that the presence or absence of a C-terminal negative charge can affect the ability of the peptide to interfere with calcium influx caused by βAP$_{25-35}$. The peptides also were synthesized with a N-terminus of either NH$_3^+$ or acetyl.

A second library was prepared using 6 D-amino acids (Ser, Thr, Leu, Ile, Val, Ala) and Gly. A third library is prepared using 5 D-amino acids: Thr, Ile, Val, Leu and Ala. The first three of these are β-C-branched amino acids, which are include based on the preference observed in screens of the first library for β-C-branched amino acids. Fourth, fifth and sixth libraries are prepared using the amino acids specified for the first, second and third libraries, with the addition of proline.

Example 4

Selection of Decoy Peptides

To select decoy peptides, fluorescently-labeled βAP$_{25-35}$ was prepared. βAP$_{25-35}$ (SEQ ID NO:10) was tagged either with FITC or DANSYL, and purified on HPLC. There was a Gly$_3$ linker separating the βAP-sequence from the fluorescent label:

FITC-GGGGSNKGAIIGLM-COOH (SEQ ID NO:11) and

DANSYL-GGGGSNKGAIIGLM-COOH (SEQ ID NO:11).

A 50 μM solution of the FITC-labeled βAP$_{25-35}$ was made in phosphate buffered saline (PBS) at room temperature and used immediately after vortexing briefly. An aliquot of 100 μL FITC-βAP$_{25-35}$ was added to a suspension of approximately 35 mg of the resin-bound hexapeptide library in 0.5 mL PBS. The suspension was very briefly vortexed 6 times during the next 15 minutes at room temperature. The beads were washed 3 times in 1 mL of PBS, spread out in a dish and examined under ultraviolet light. Of the thousands of beads present in the dish, only very few were brightly fluorescent. Only the surface of the beads were fluorescent, indicating that the FITC-βAP$_{25-35}$ had not penetrated the beads. Brightly fluorescent beads were picked and transferred with fine forceps onto glass filters for sequencing.

In a similar fashion, beads from the same library were selected using DANSYL-labeled βAP$_{25-35}$. In that case, 12 μM solution of Dansyl-βAP$_{25-35}$ in PBS was used. Blue fluorescent beads were picked out and sequenced as above.

Most of the D-amino acid containing hexapeptides with a Gly$_3$ tail selected from this first library begin with a β-branched amino acid. This may indicate a relationship between the β-sheet forming strength and the number of β-branched amino acids.

The following sequences were obtained and the corresponding peptides were synthesized using D-amino acids. The peptides were synthesized with a carboxyl terminus of either —COOH or —CONH$_2$.

TABLE 2

Synthetic D-Amino Acid Decoy Peptides

| | SEQ ID NO | C-TERMINUS —COOH | —CONH$_2$ |
|---|---|---|---|
| FITC-βAP-SELECTED | | | |
| $^+$NH$_3$.I.A.A.G.I.T.G.G.G | SEQ ID NO:1 | DP(1) | |
| $^+$NH$_3$.T.V.I.G.T.I.G.G.G | SEQ ID NO:2 | DP(2) | DP(3) |
| $^+$NH$_3$.T.G.I.I.A.S.G.G.G. | SEQ ID NO:3 | DP(4) | DP(5) |
| $^+$NH$_3$.V.V.I.S.G.A.G.G.G | SEQ ID NO:4 | | |
| $^+$NH$_3$.V.V.I.S.A.A.A | SEQ ID NO:12 | DP(21) | |
| DANSYL-βAP-SELECTED | | | |
| $^+$NH$_3$.T.T.I.V.S.T.G.G.G | SEQ ID NO:5 | DP(6) | |
| $^+$NH$_3$.A.G.V.I.S.I.G.G.G | SEQ ID NO:6 | DP(7) | |
| $^+$NH$_3$.I.G.A.S.I.V.G.G.G | SEQ ID NO:7 | | |
| $^+$NH$_3$.S.I.A.T.S.T.G.G.G | SEQ ID NO:8 | | |
| $^+$NH$_3$.I.A.A.S.I.V.A | SEQ ID NO:13 | DP(22) | |
| $^+$NH$_3$.S.I.A.T.S.T.A | SEQ ID NO:14 | DP(23) | |
| Decoy Peptide Derived from DP(3) | | | |
| T.V.I.R$^+$.T.I.A.A.A | SEQ ID NO:9 | DP(8) | |

β-sheet forming potential ([s]) of each peptide was assessed using the Chou-Fasman algorithm:
X = [s] barely above 1
X = [s] above 1
X = [s] much above 1.

DP(n) is the decoy peptide number, assigned when peptides were synthesized.

An assessment of β-sheet forming ability was made by the Chou-Fasman algorithm using "Peptide Companion" software, version 1.24. For example, DP1 ($^+$NH$_3$-IAAGITGGG-COO$^-$; SEQ ID NO:1) has a moderate β-sheet forming potential. DP2 ($^+$NH$_3$-TVIGTIGGG-COO$^-$; SEQ ID NO:2) and DP3 ($^+$NH$_3$-TVIGTIGGG-CONH$_2$; SEQ ID NO:2) each of which contains only D-amino acids, have strong β-sheet forming potential centered on the N-terminal TVI sequence.

A peptide derived from DP3, DP8, which is $^+$NH$_3$-TVIR$^+$TIAAA-COO$^-$(SEQ ID NO:9) has been synthesized and tested. Without affecting β-sheet forming potential, this change introduces a charged side chain into the middle of the sequence which may affect the function of the β-sheet structure that could form when DP8 and βAP$_{25-35}$ aggregate together. Replacing glycine at the fourth position of the decoy peptide DP3 with glutamic acid is predicted to reduce the β-sheet forming potential and was not used.

Example 5

Activity of Decoy Peptides—Calcium Influx

Figure 5:
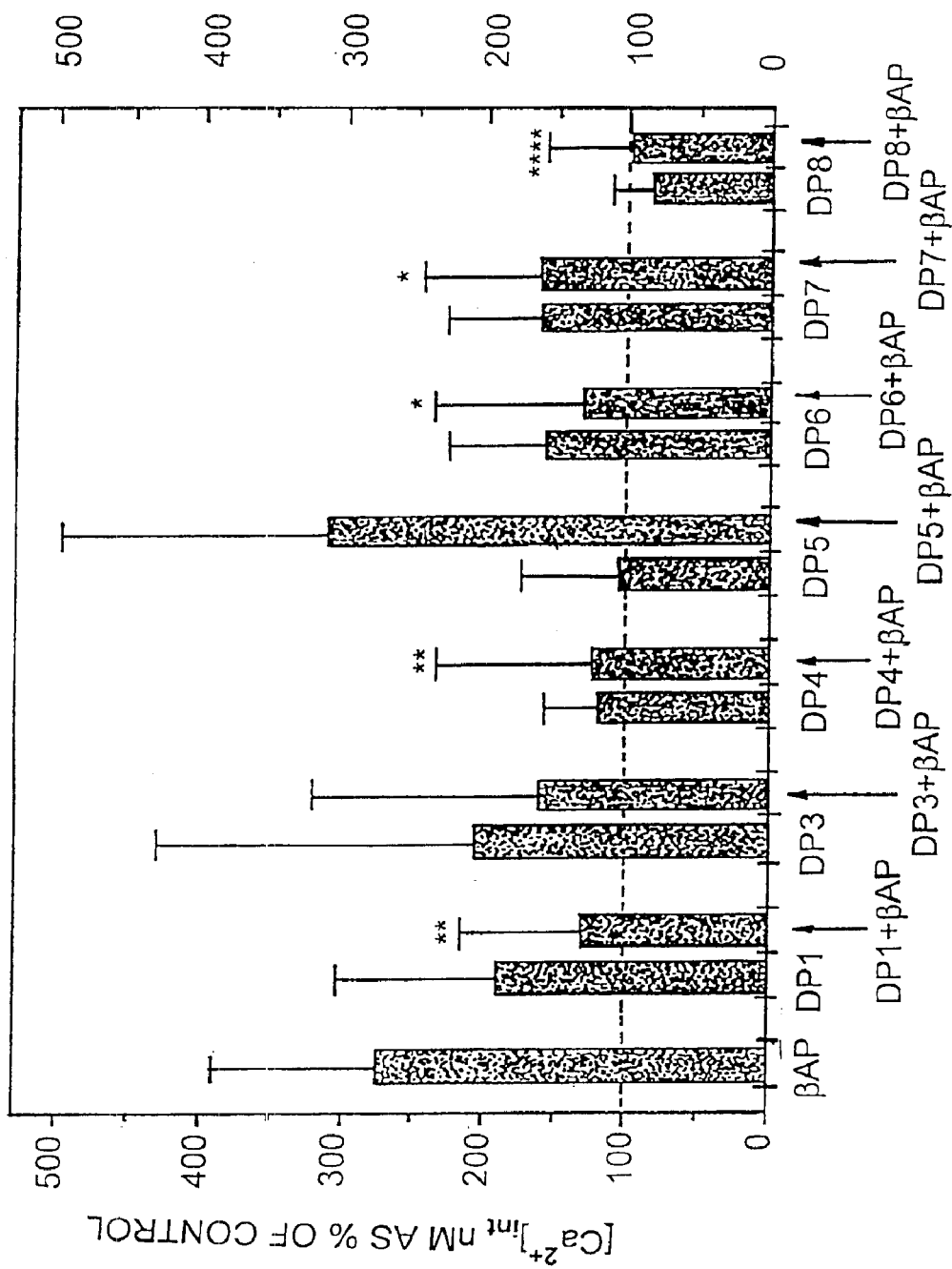
FIG. 5 is a bar graph which shows that decoy peptides can reduce the $\beta AP_{25-35}$-induced $Ca^{2+}$ influx at a 1:1 molar ratio.

Decoy peptides were tested for the ability to reduce or prevent calcium influx in hNT cells in the presence or absence of βAP$_{25-35}$. Decoy peptides (except for DP1, which is water soluble) and βAP$_{25-35}$ were prepared as DMSO stocks at approximately 50 mM, spin filtered through a 30,000 MW cut-off Millipore filter (cat. no. UFC3LTK00), aliquoted and stored at −40° C. Decoy peptides (DP1, DP3–DP8) were diluted in Tyrode's/2 mM Ca or mixed with βAP$_{25-35}$/Tyrode's/2 mM Ca at a ratio of 1:1 (20 μM+20 μM). The decoy peptide or peptide mixtures were added to HNT cells preloaded with fura-2, and change in the internal calcium concentration was detected. The results are depicted in FIG. 5. The significance of the difference of certain means from the mean [Ca$^{2+}$]$_{int}$ due to βAP$_{25-35}$ treatment is expressed as: *$P<0.05$; $P<0.01$; **$P<0.0001$.

Unexpectedly, the decoy peptides DP1, DP3, DP6 and DP7 by themselves at 20 µM concentration raise cytosolic calcium concentrations somewhat, though not nearly as much as does 20 µM βAP$_{25-35}$ On the other hand, DP4, DP5 and DP8 have no effect on cytosolic calcium concentrations when added alone to hNT cells. When added with βAP$_{25-35}$, decoy peptides DP1, DP3, DP4, DP6, DP7 and DP8 reduced or abolished the increase in the internal calcium concentration due to βAP$_{25-35}$, and were considered suitable candidates for further testing.

Figure 6:
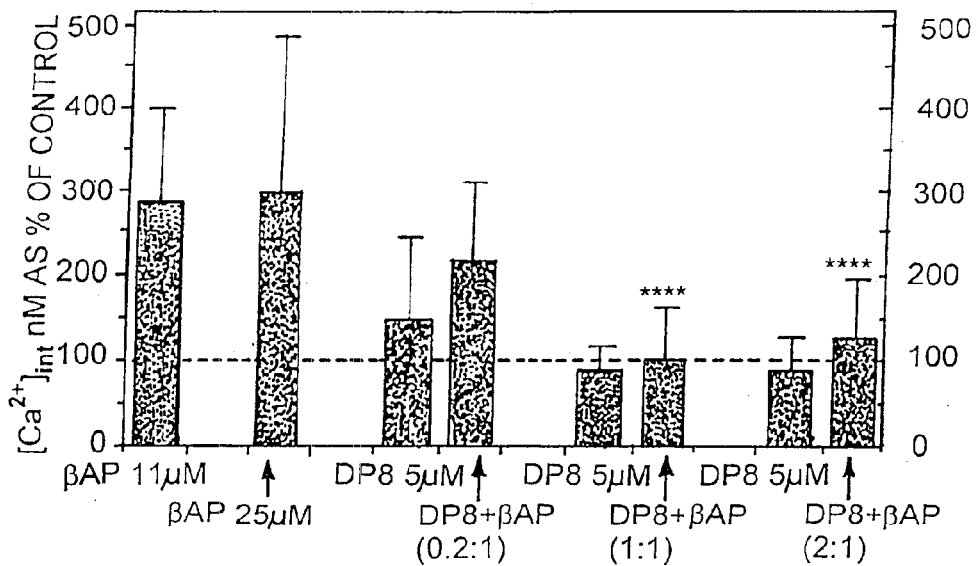
FIG. 6 is a bar graph which shows the effect of the decoy peptide DP8 on $\beta AP_{25-35}$-induced $Ca^{2+}$ influx at several molar ratios.

FIG. 6 shows the effect of the addition of DP8 to βAP$_{25-35}$ at several different molar ratios. DP8 was only used from filtered DMSO stocks. Each column represents the mean [Ca2+]int of 9–31 cells±S.D. The molar ratios of DP8:βAP$_{25-35}$ were 0.2:1 (5 mM DP8+20 mM βAP25-35), 01:1 (10 mM DP8+10 mM βAP$_{25-35}$), and 2:1 (20 mM DP8+11 mM βAP$_{25-35}$). The significance of the experimental means from the mean of βAP$_{25-35}$ treatment is expressed as ****P<0.0001. At a ratio of DP8:βAP$_{25-35}$ of 0.2:1 calcium influx was modestly reduced. However, at molar ratios of 1:1 or 2:1, the decoy peptide DP8 was able to reduce or abolish the effect of the β-amyloid peptide.

Figure 7:
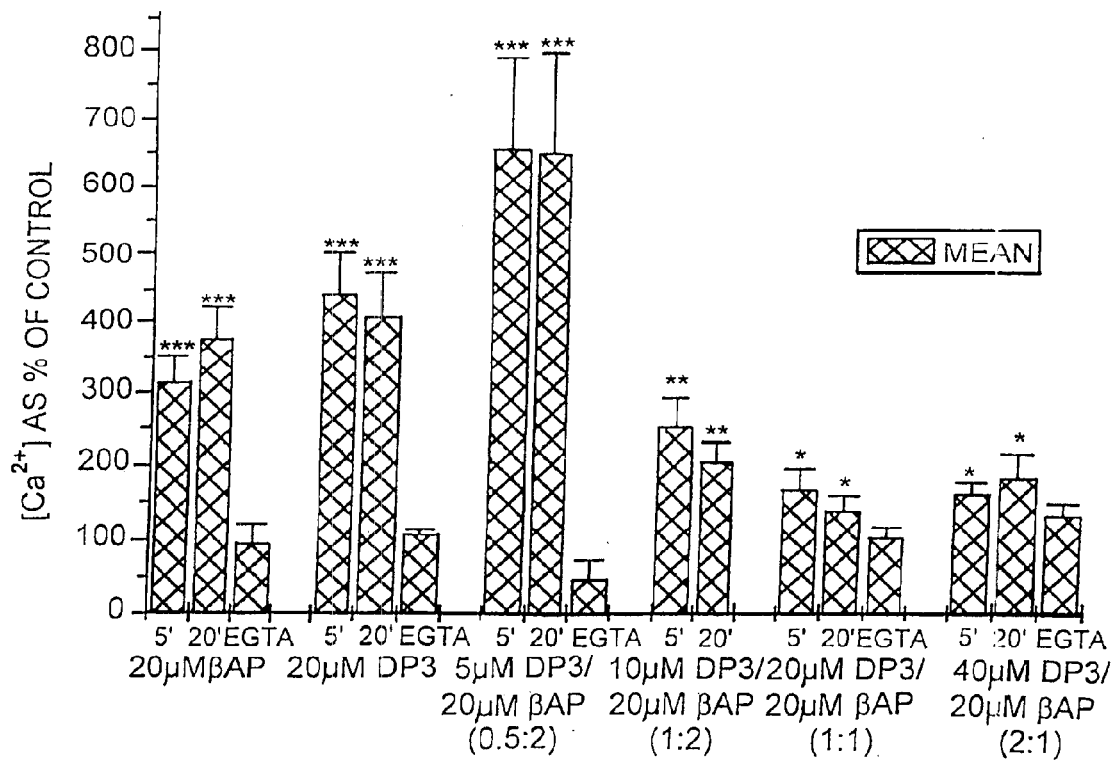
FIG. 7 is a bar graph which shows the effect of the decoy peptide DP3 on $\beta AP_{25-35}$-induced $Ca^{2+}$ influx at several molar ratios.
Figure 8:
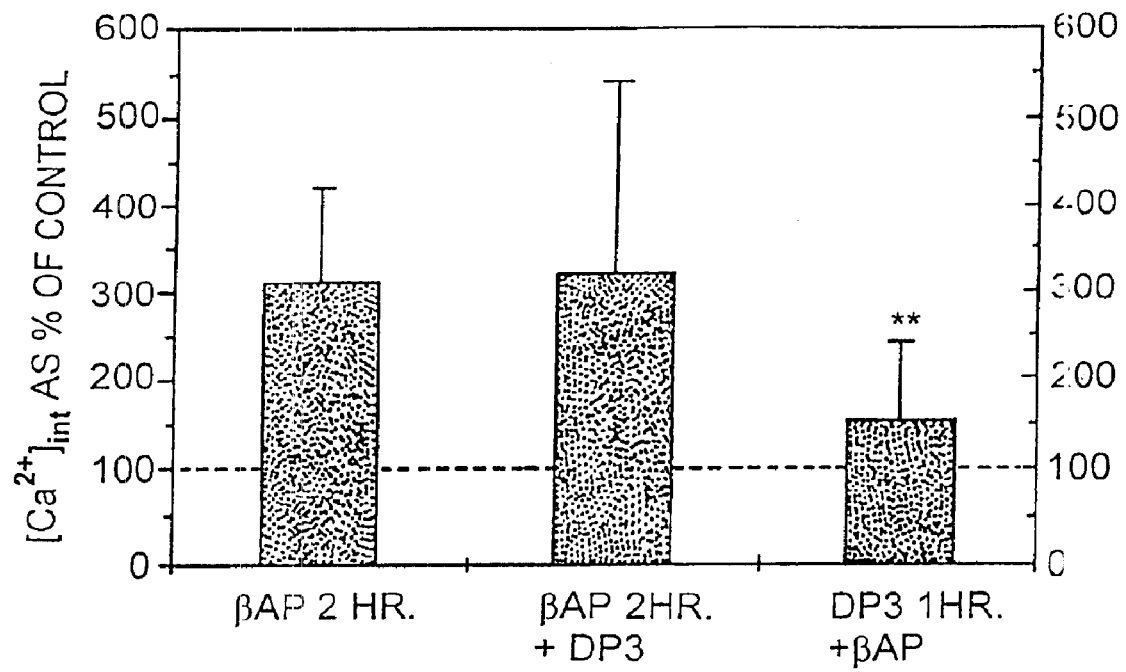
FIG. 8 is a bar graph which shows that DP3 can reduce the $\beta AP_{25-35}$-induced $Ca^{2+}$ influx when added to $\beta AP_{25-35}$ prior to aggregation.
Figure 9A:
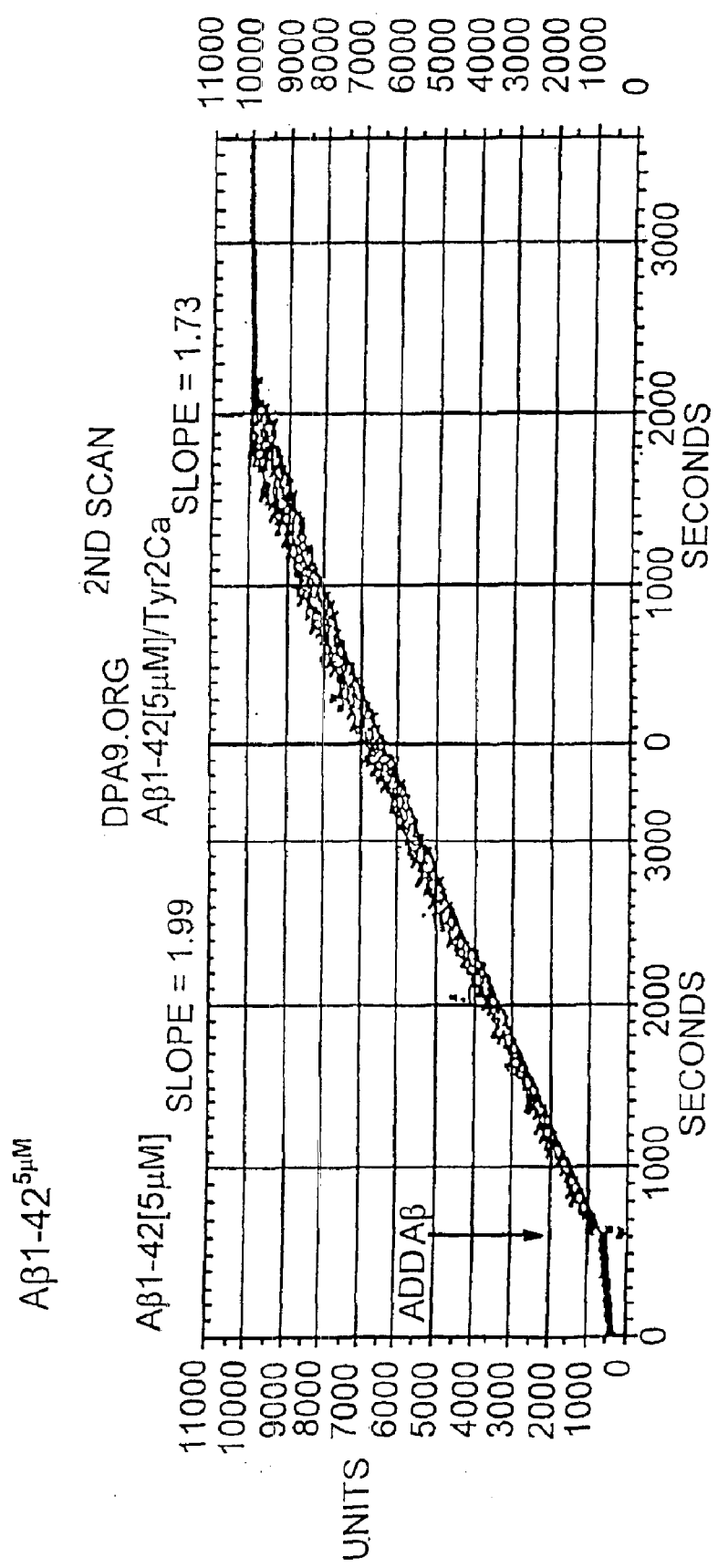
Figure 9B:
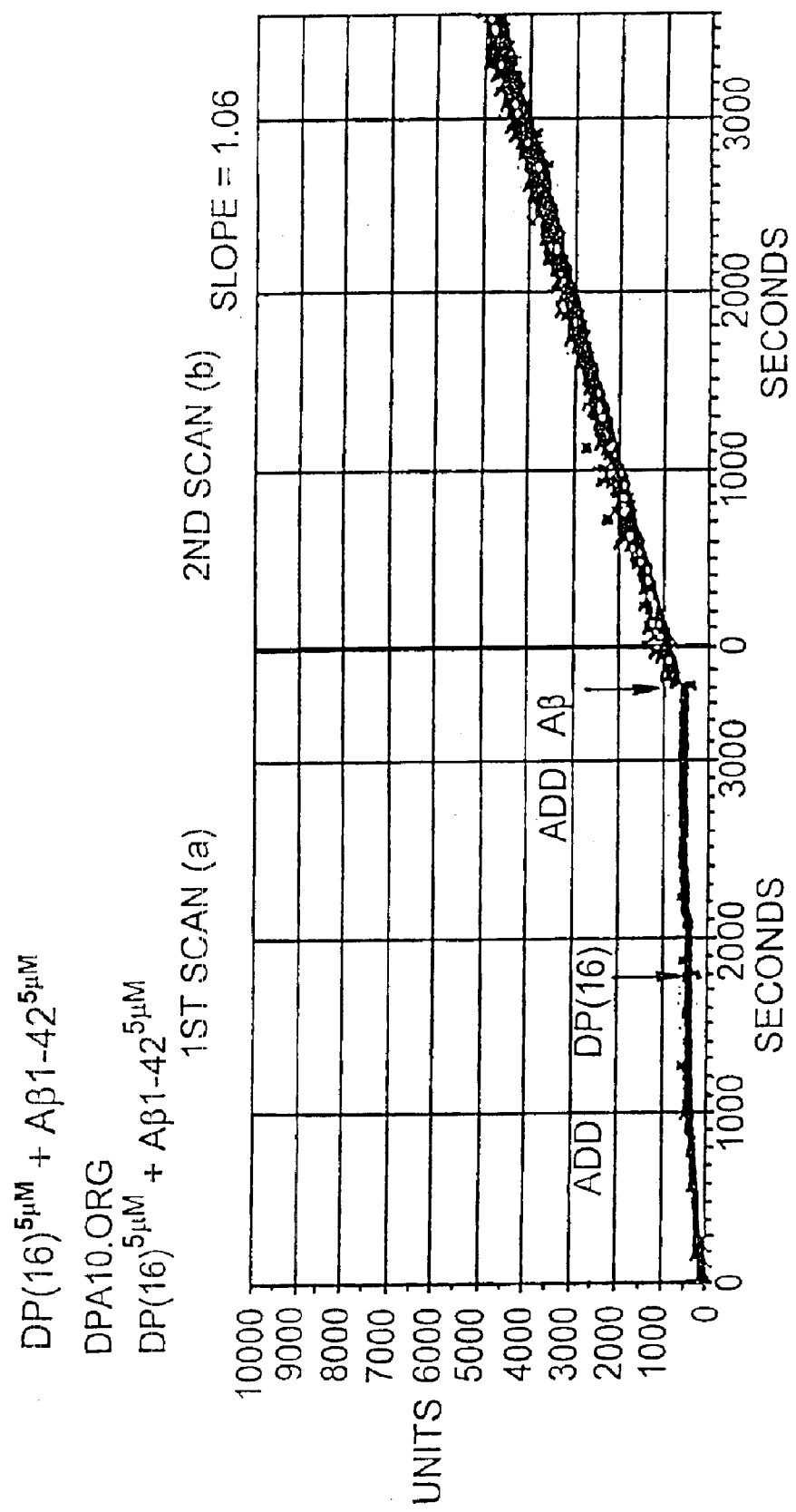
Figure 9C:
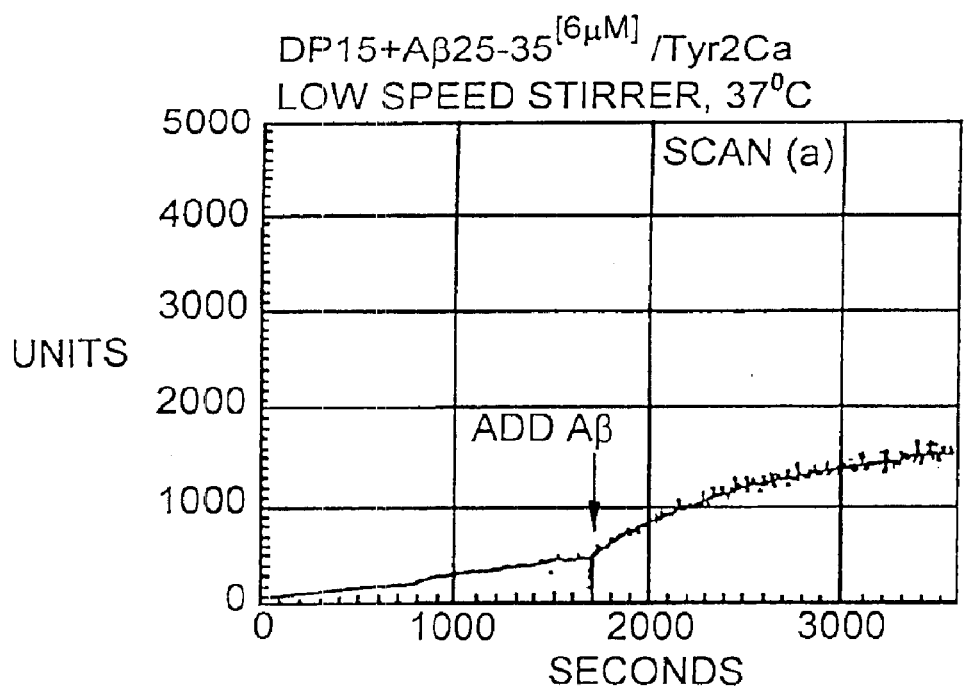
Figure 9D:
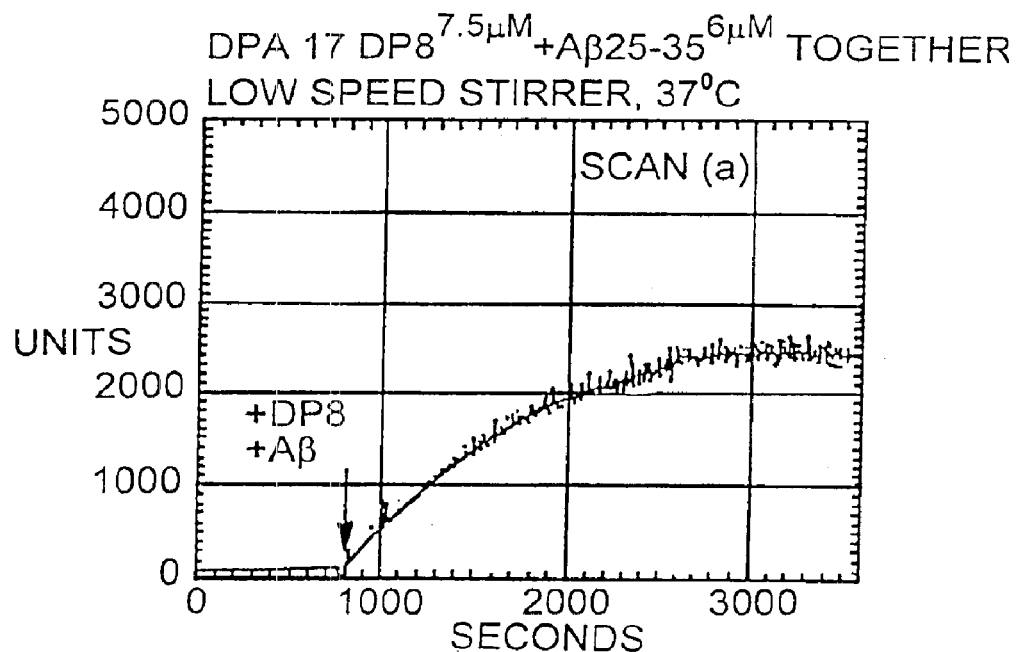
Figure 9E:
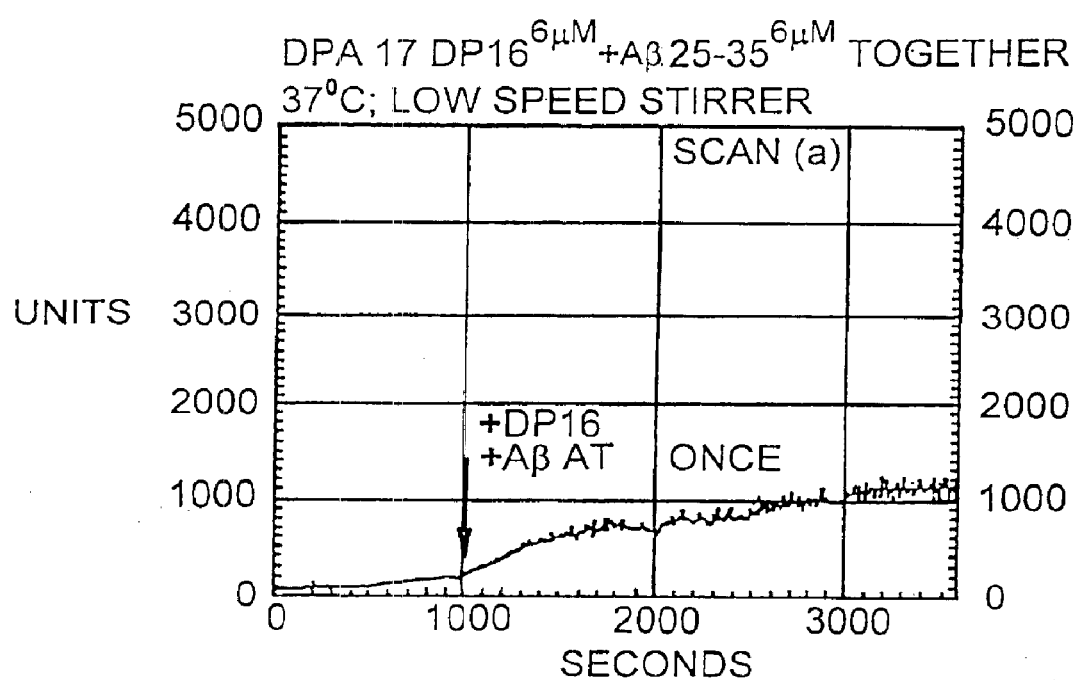

FIG. 7 shows the effect of the decoy peptide DP3 at several molar ratios on internal calcium concentrations induced by βAP$_{25-35}$. In this experiment, the DP3 stock was not filtered. Each column graph in FIG. 7 represents the mean [Ca$^{2+}$]$_{int}$ of 6–12 cells measured as described above. Each group of three columns represents a single dish with measurements after application of DP3+βAP$_{25-35}$ in Tyrode's/2 mM Ca at approximately 10 minutes, and after 20 µM EGTA was added within 2 minutes.

When the unfiltered DP3 peptide was added to hNT cells at 20 µM (control, second group of columns from left), there was an increase in [Ca$^{2+}$]$_{int}$. However, when decoy peptide DP3 from unfiltered stocks and βAP$_{25-35}$ were mixed at molar ratios of 1:2 or greater, the marked decrease in the ability of βAP$_{25-35}$ to induce influx of calcium was observed. This effect became more marked as the proportion of decoy peptide increased.

Example 6

Activity of Decoy Peptides—Aggregation of βAP

Decoy peptides were tested for the ability to alter the aggregation of βAP$_{25-35}$. FIG. 6 shows the effect of adding decoy peptide DP3 to aggregated βAP$_{25-35}$. Each column represents the mean [Ca2+]int of 9–13 cells±S.D. DP3 and βAP$_{25-35}$ were both used at 20 mM. The first column shows βAP$_{25-35}$ after aggregation for 2 hours at room temperature. In the experiment resulting in the second column, βAP$_{25-35}$ was allowed to aggregate for 2 hours prior to the addition of DP3. The third column shows the results when DP3 was diluted into Tyrode's/2 mM Ca, allowed to stand for 1 hour, and βAP$_{25-35}$ was subsequently added. The significance of the differences of the mean of the third column relative to βAP$_{25-35}$ measurements is **P<0.01. Therefore, addition of DP3 after βAP$_{25-35}$ has aggregated did not reduce the induction of calcium influx by βAP$_{25-35}$. Addition of DP3 prior to βAP$_{25-35}$ aggregation reduced the calcium influx induced by βAP$_{25-35}$. These results suggest that decoy peptide such as DP3 can interfere with the aggregation of β-amyloid peptides such as βAP$_{25-35}$ in a manner which inactivates the induction of calcium influx by the β-amyloid peptide.

Decoy peptides were tested for the ability to alter the aggregation kinetics of β-amyloid peptides such as βAP$_{1-42}$ or βAP$_{25-35}$. The aggregation rate of βAP$_{1-42}$ and βAP$_{25-35}$ was determined alone (panels A and C, respectively) and in the presence of decoy peptides DP8 (panel D) and DP16 (panels B and E). Light scattering of βAP$_{1-42}$ or βAP$_{25-35}$ in Tyrode's/2 mM Ca$^{2+}$ was measured at 500 nm using a Hitachi F4500 fluorescence spectrophotometer (Hitachi instruments, San Jose, Calif.). As shown in FIG. 9, DP16 added at a 1:1 molar ratio reduced the aggregation rate of βAP$_{1-42}$ by about 50% (compare panels A and B) and reduced the aggregation rate of βAP$_{25-35}$ (compare panels C and E) while DP8 added at an approximately equimolar concentration did not reduce the aggregation rate of βAP$_{25-35}$ (compare panels C and D). DP8 may act by being incorporated into the β-amyloid fibril and disrupting the interaction of the fibril with the cell to reduce calcium influx.

Other methods for testing aggregation of βAPs include binding of thioflavine T (ThT) (e.g., LeVine, *Protein Sci* 2:404–410, 1993), binding of Congo Red and additional light scattering techniques (e.g., Shen et al., *Biophys J.* 65:2383–2395, 1993; Tomski and Murphy, *Arch Biochem. Biophys.* 294:630–638, 1992) and negative staining in the electron microscope.

Example 7

Preparation of Variant Decoy Peptides

Based on the decoy peptides identified above, variant decoy peptides were prepared by substituting one or more amino acids, eliminating amino acids, and/or substituting N-terminal (e.g. acetyl (Ac) for NH$_3^+$) and/or C-terminal moieties (e.g. CONH$_2$ for COO$^-$). Variant decoy peptides were synthesized using standard peptide synthesis equipment, following standard chemistries. Substituted decoy peptides were tested for β-sheet forming ability by the Chou-Fasman algorithm using Peptide Companion software. In addition to applying the Chou-Fasman rules, solubility and aggregating properties of the decoy peptides were taken into account.

TABLE 3

Modified D-Amino Acid Decoy Peptides

| PEPTIDE SEQUENCE | DECOY PEPTIDE # | SEQ ID NO |
|---|---|---|
| $^+$NH$_3$.T.V.I.R$^+$.T.I.COO$^-$ | DP(12) | 15 |
| $^+$NH$_3$.T.V.I.R$^+$.T.COO$^-$ | DP(13) | 16 |
| Ac.NH.T.V.I.R$^+$.T.I.CONH$_2$ | DP(14) | 15 |
| Ac.NH.T.V.I.R$^+$.T.CONH$_2$ | DP(15) | 16 |
| $^+$NH$_3$.T.P.I.R$^+$.T.P.A.P.A.COO$^-$ | DP(16) | 17 |
| $^+$NH$_3$.P.V.P.R$^+$.P.I.P.A.P.COO$^-$ | DP(17) | 18 |
| $^+$NH$_3$.T.P.I.R$^+$.T.P.A.COO$^-$ | DP(20) | 19 |
| $^+$NH$_3$.T.P.I.R$^+$.T.P.A.P.A.CONH$_2$ | DP(25) | 17 |
| Ac.NH.T.P.I.R$^+$.T.P.A.P.A.COO$^-$ | DP(26) | 17 |

DP(12)–DP(17) were designed based on the sequence of DP(3) and DP(8). DP(20), DP(25) and DP(26) were designed based on the sequence of DP(16).

The effectiveness of the substituted decoy peptides in inhibiting the formation of neurotoxic β-amyloid peptide aggregates and/or affecting neuronal calcium influx mediated by non-NMDA cation channels was tested as described above in Example 5.

FIG. 10 shows the effect of decoy peptides DP8, DP16 and DP17 on the influx of calcium due to exposure of hNT cells to βAP$_{1-42}$. βAP$_{1-42}$ (designated here as Aβ1-42) at 25 µM was coincubated with an equimolar concentration of the decoy peptides at 37° C. for 44 hours. The mixtures were then applied to hNT cells and [Ca$^{2+}$]$_{int}$ measured as described above. FIG. 10 shows that DP8 and DP16 reduced or abolished the effect of βAP$_{1-42}$ on the calcium influx. DP17 did not reduce the effect of βAP$_{1-42}$ on the calcium influx.

Still other decoy peptides were prepared or selected according to the above-described procedures and are tested for activity as described herein.

TABLE 4

Additional Decoy Peptides

| PEPTIDE SEQUENCE | DECOY PEPTIDE # | SEQ ID NO |
|---|---|---|
| $^+$NH$_3$.S.T.I.T.A.CONH$_2$ | DP(27) | 22 |
| $^+$NH$_3$.S.S.S.T.A.CONH$_2$ | DP(28) | 23 |
| $^+$NH$_3$.S.A.P.A.A.CONH$_2$ | DP(29) | 24 |
| $^+$NH$_3$.L.P.V.L.A.CONH$_2$ | DP(30) | 25 |
| $^+$NH$_3$.L.P.V.S.A.CONH$_2$ | DP(31) | 26 |
| $^+$NH$_3$.L.P.T.S.A.CONH$_2$ | DP(32) | 27 |
| $^+$NH$_3$.S.S.T.V.P.A.CONH$_2$ | DP(33) | 28 |
| $^+$NH$_3$.S.S.A.P.P.A.CONH$_2$ | DP(34) | 29 |
| $^+$NH$_3$.S.S.T.V.T.A.CONH$_2$ | DP(35) | 30 |

Additional variant peptides are prepared according to the procedures described above.

Another consideration for designing variant decoy peptides is the potential toxicity of such peptides in vivo. Given an effective but toxic decoy peptide, the amino acid sequence, N-terminal groups and/or C-terminal groups can be modified systematically to prepare a peptide of lesser toxicity, for example by adding, eliminating or substituting end groups or one or more amino acids of the peptide. Upon preparation of one or more of such peptides, the peptides can be tested individually in an appropriate in vivo setting, such as animal studies in mammals, to determine whether the toxicity has been reduced by the one or more modifications to the peptide. Preferably the animal studies are conducted in a model system, such as transgenic mice that express β-amyloid precursor protein, in which the combination of efficacy against neurotoxicity and a lack of toxicity can be assessed.

Example 8

Selection of Decoy Peptides Using βAP$_{1-42}$

A peptide library containing proline was prepared as described in Example 3. The library included amino acids Ser, Pro, Ala, and Leu. Peptides were selected from the library using the selection procedure described in Example 4, except that βAP$_{1-42}$ (SEQ ID NO:20) was used as the fluorescently labeled binding target for the peptides in the library. As an example, the peptide S.P.A.L.A (SEQ ID NO:21) was isolated and synthesized with two different C-termini: $^+$NH$_3$.S.P.A.L.A.COO$^-$(DP(18)) and $^+$NH$_3$.S.P.A.L.A.CONH$_2$(DP(19)). These peptides are tested as described above in Example 5. Variants of this peptide and other peptides selected from the second peptide library can be designed and prepared as described above using only routine experimentation.

Example 9

βAP$_{1-42}$ Aggregates Increase Neuronal Cell Depolarization

Aβ1-42 Sample Preparation

Aβ1-42 (formerly known as βAP$_{1-42}$) was obtained from Quality Controlled Biochemicals, Inc. (Hopkinton, Mass.). Two particular batches of the peptide were used. A stock solution of Aβ1-42 (1 mM) was made in double-distilled, deionized water adjusted to pH 9 with 1M ammonium hydroxide and stored in aliquots at −40° C. until use. Experimental samples were prepared by diluting stock Aβ1-42 to 10 μM (unless otherwise noted) in Tyrode's/2mMCa buffer (pH 7.4).

Fura-2 Measurements of Internal Calcium Concentration

The UV-excitable, ratiometric Ca$^{2+}$ indicator fura-2 was used in its cell permeant form fura-2AM (Molecular Probes, Inc., Eugene, Oreg.). Measurements of internal calcium concentration were carried out on human neuronal hNT cells, a human teratocarcinoma cell line differentiated with retinoic acid with many neuronal properties (Stratagene, Inc., La Jolla, Calif.), following the methods and statistical analysis as previously described (Blanchard et al., *Brain Res.* 776:40–50, 1997; B. J. Blanchard, A. E. Hiniker, C. C. Lu, Y. Margolin, V. M. Ingram, (2000) *J Alzheimer Disease* Vol. 2, No. 2 (in press)). Unless otherwise indicated, all measurements were carried out in Tyrode's solution containing 2 mM Ca.

Membrane Potential Measurements

Changes in membrane potential were measured using the fluorescent potentiometric probe DiBAC$_4$(3), (Molecular Probes, Inc., Eugene, Oreg.). This dye, bis-(1,3-dibutylbarbituric acid)trimethine oxonol, detects membrane depolarization, because it enters depolarized cells and binds to intracellular proteins or membranes. The bound dye exhibits enhanced fluorescence and red spectral shift (Hartinger and Jahn, *J. Biol. Chem* 268:23122–23127, 1993; Cooper et al., *Biochemistry* 29:3859–3865, 1990). Hyperpolarization results in extrusion of the anionic dye and thus a decrease in fluorescence. Our measurements use two dyes, fura-2 and DiBAC$_4$(3), since these dyes have excitation wavelengths that are far apart, but have similar emission wavelengths. DiBAC$_4$(3) was added to fura-2AM loaded hNT cells at a concentration of 100 nM in Tyr2Ca. Rapidly alternating measurements of fura-2 (excited at 340 & 380 nm) and DiBAC$_4$(3) (excited at 490 nm) were performed using emission at 516 nm. Both dyes were measured using the special "Fura2-Fluo3" filter set 7400 from Chroma Technology (Brattleboro, Vt.), a Zeiss Axiovert 100 inverted microscope and a photometry system (model "Delta Ram" from Photon Technology International, Inc., Monmouth Junction, N.J.).

To ensure that the presence of each dye did not interfere with the readings from the other dye, calcium calibrations were performed with fura-2 salt alone and with fura-2 salt+DiBAC$_4$(3). "Fura-2 salt" is the water soluble sodium salt of fura-2, corresponding to the cytosolic hydrolysis product of the cell-permeant AM-ester with which the cells had been loaded and which is generated by hydrolysis during the short recovery phase after cell loading. The presence of DiBAC$_4$(3) to the fura-2 calcium calibration showed no significant interference.

The bis-oxonol dye DiBAC$_4$(3) was used as an indicator of transmembrane electrical potential changes (Langheinrich and Daut, *J. Physiol.* 502:397–408, 1997) when our hNT cells were treated with, for example, the β-amyloid peptide Aβ1-42. The use of this dye enabled us to monitor groups of 5–15 neurons, rather than single cells as would be the case with patch clamping methods. We expected great variability from cell to cell, as was found in our earlier patch clamp work (Sanderson et al., *Brain Res.* 744:7–14, 1997). The method has been used by many laboratories for the determination of membrane potentials in different cell types. Fluorescence is increased upon membrane depolarization as more dye enters the cytosol, resulting in increased binding to proteins (Braiuner et al., *Biochim. Biophys. Acta* 771:2208–216, 1984). Partitioning of bis-oxonol dye between the plasma membrane and the cytosol follows the Nernst equation (Langheinrich and Daut, 1997). Unless otherwise indicated, all measurements were carried out in Tyrode's solution containing 2 mM Ca.

We calibrated the gross fluorescence as a function of membrane potential by treating a culture of hNT neurons, bathed in Tyrode's 2Ca buffer with the usual 3 mM K$^+$, containing 97 nM DiBAC$_4$(3), with Tyrode's 2Ca buffer containing 40 mM KCl. We measured the gross fluorescence at excitation=490 nm and emission=510 nm for the depolarization by KCl and for depolarization by the Aβ1-42 peptide. We used the formula proposed by Langheinrich and Daut, 1997:

$$\% \Delta F = (1 - F_{min}/F_{max}) * 100 = \Delta E_M \text{ mV}$$

where $F_{min}$=fluorescence before treatment, $F_{max}$=fluorescence during treatment, $\Delta E_M$ mV is the change in membrane potential brought about by the treatment. The calculation based on the expected depolarization by changing from 3 mM KCl to 40 MM KCl gave a value of $\Delta E_M$=3.8 mV/1% $\Delta F$.

Aggregated Aβ1-42 Induces Membrane Depolarization

Addition of the pre-aggregated Aβ1-42 β-amyloid peptide (Aβ1-42aggr) to cultured hNT neuronal cells caused a large membrane depolarization in the cells. Groups of hNT cells, loaded with fura-2 and in Tyrode's/2Ca buffer containing DiBAC$_4$ (3), were exposed to aggregated Aβ1-42 for approximately 1,200 seconds. In the presence of the slow-acting voltage-sensitive fluorescent dye DiBAC$_4$(3), there was an immediate sharp increase in fluorescence to a high plateau when Aβ1-42aggr was added (FIG. 11A), indicating cell membrane depolarization. The new plateau was moderately stable for at least 1,000 seconds, and often longer, but fluctuations sometimes were observed. CNQX, an AMPA/kainate antagonist, was then added and was also present for the next ~1,000 seconds. There was little change in fluorescence; the sharp peak in fluorescence is unexplained. Replacing the buffer with Tyrode's/2Ca also did not change the fluorescence plateau appreciably.

To measure cytosolic calcium concentrations, the hNT cells were loaded with the ratiometric calcium dye fura-2. Therefore, we were able to observe in the same experiment a large increase in cytosolic calcium as well as the membrane depolarization upon addition of aggregated Aβ1-42 to the cells (FIG. 11B). However, the cytosolic calcium level began at once to decrease spontaneously (desensitization), whereas the depolarization remained at a plateau. In other experiments where a longer time was allowed, the calcium level settled to a new plateau value, about twofold higher than control values (see Blanchard et al., 1997, Blanchard et al., 2000). It should be noted that the rate of decrease is very much slower than the usual rate of desensitization of, for example, AMPA channels. It is likely that the rapid influx of calcium activates the processes that normally keep cytosolic calcium levels very low, e.g. ATP-powered calcium pumps that either sequester calcium or pump it out of the cell. The end result seems to be an equilibrium between influx of calcium and pumping out/sequestering calcium.

The remaining calcium influx was completely inhibited by 20 μM CNQX, and as a result cytosolic calcium immediately decreased to control levels upon addition of CNQX. The addition of CNQX, a specific AMPA/kainate receptor blocking agent, reduced the cytosolic calcium level to close to the control value at the beginning of the experiment (FIG. 11B). For that reason we believe that AMPA/kainate channels are involved in the influx of calcium. However, the membrane depolarization plateau remained unchanged (FIG. 11A).

The effect of NMDA on calcium influx also was tested. The NMDA blocker D-AP5 was added at a concentration of 50 μM to cells with aggegated Aβ1-42 (see FIG. 13). D-AP5 addition largely, but not completely, abolished calcium influx. As with CNQX, D-AP5 did not interfere with the depolarization phenomenon (FIG. 13A). After washout and replacement of the external solution with just aggregated Aβ1-42, the membrane potential remained depolarized at a slightly higher level than control. The simultaneous fura-2 measurements (FIG. 13B) indicate that D-AP5 inhibited much of the calcium influx, allowing only a late rise in cytosolic calcium. After washout and replacement of aggregated Aβ1-42 there was the expected sharp rise in cytosolic calcium, which then slowly declined, as usual.

The presence of the specific sodium channel blocker tetrodotoxin (TTX) allowed both membrane depolarization and a rise in cytosolic calcium levels when pre-aggregated Aβ1-42 was added to the cells (FIG. 4). Similarly, cadmium chloride, which blocks voltage-gated calcium channels, did not prevent membrane depolarization by aggregated Aβ1-42 (data not shown). Thus, voltage-gated sodium channels were not involved in causing either the membrane depolarization or the influx of calcium ions.

Arispe et al. have reported (*Proc. Natl. Acad. Sci. USA* 90:567–571, 1993) that the β-amyloid peptide Aβ1-40 forms a cation ionophore in artificial membranes and that this can be blocked by 10 mM TRIS$^+$. To determine whether the observed membrane depolarization is due to a similar ionophore effect, but using Aβ1-42, we exposed hNT neuronal cells to Aβ1-42 aggregates in the absence and then in the presence of 10 mM TRIS$^+$. We found a moderate decrease in membrane depolarization at 10 mM TRIS$^+$ (FIG. 12).

To test whether increased cytosolic calcium is from internal or external sources, the hNT cells were placed in Tyrode's buffer with different calcium concentrations (Table 1). Increasing external calcium from 2 mM to 10 mM made no difference to the membrane potential; however, the calcium influx became very large indeed (data not shown). Decreasing external calcium to 0.4 mM decreased the membrane potential increase somewhat, but did not eliminate it (Table 1). When calcium was entirely left out of the external medium, a remarkably large increase in fluorescence was seen (FIG. 15; Table 1). We have no explanation for these last two observations. It is, of course, well known that neuronal cells need external calcium for morphological, and perhaps for membrane stability.

To test whether other external ions could take the place of Na$^+$ in the Tyrode's buffer solution and still cause depolarization, external Na$^+$ was replaced with an equal concentration of either tetraethylammonium$^+$ (TEA$^+$) or N-methyl-D-glucamine$^+$ (NMDG$^+$). These ions also allowed Aβ1-42 to cause a large membrane depolarization (FIG. 16A,B). When TEA$^+$ was used, cytosolic calcium also rose sharply as expected and then decreased (FIG. 16A'). In this particular experiment the cytosolic calcium level dipped spontaneously and quickly from the initial high value almost to control values, but then rapidly recovered to the expected high values. We have no explanation for this behavior, but have observed it on several occasions. In the TEA$^+$ experiment, depolarization was partially reversible, when the peptide was washed out (FIG. 16A). When Aβ1-42 was added to cells in Tyrode's buffer containing NMDG$^+$ (FIG. 16B) instead of Na$^+$, there was again a sharp membrane depolarization, as well as a strong increase in cytosolic calcium. However, we did not observe in this experiment a sharp initial calcium spike.

TABLE 1

Depolarization Effect of Aggregated Aβ1-42

| Fig. # | [Ca$^{2+}$] mM | ext. Cat. | Addition | % ΔF | Δ E$_M$ mV |
|---|---|---|---|---|---|
| FIG. 1 V102 | 2 | Na$^+$ | — | 15.7 | +59.7 |
| FIG. 2 V123 | 2 | Na$^+$ | — | 14.8 | +65.2 |
| — | 0.4 | Na$^+$ | — | 8.3 | +31.6 |
| — | 10 | Na$^+$ | — | 15.3 | +58.3 |
| FIG. 1 V102 | 2 | Na$^+$ | CNQX | 17.0 | +64.6 |
| FIG. 3 V091 | 2 | Na$^+$ | D-AP5 | 10.4 | +39.5 |
| FIG. 4 V082 | 2 | Na$^+$ | TTX | 17.3 | +65.7 |
| FIG. 5 b712 | 0 | Na$^+$ | — | 51.1 | * |
| FIG. 6A b677 | 2 | TEA$^+$ | — | 44.8 | * |
| FIG. 6B b756 | 2 | NMDG$^+$ | — | 44.1 | * |

*In these experiments the % ΔF is very large; the described method for deriving ΔE$_M$ may not apply.

Groups of hNT neuronal cells (5–17) were exposed to Aβ1-42 (20 μM) that had been incubated at 37° C. for 48 hours; 97 nM DiBAC$_4$(3) was present. Fluorescence was measured as described above; Ex=490 nm, Em=510 nm.

According to the results shown above, the membrane depolarization by aggregated Aβ1-42 is not inhibited by the simultaneous presence of the ion channel blockers CNQX or D-AP5, separately or together. These findings distinguish the mechanism for membrane depolarization from the mechanism for calcium influx, since the latter phenomenon is inhibited by CNQX and by D-AP5. Membrane depolarization by aggregated Aβ1-42 is not dependent on external Ca$^{2+}$. Presumably it is caused by an influx of cations through an ionophore formed by the peptide (see Arispe, et al., Proc. Natl. Acad. Sci. USA 90: 567–571, 1993a; Arispe et al., Proc. Natl. Acad. Sci. USA 90: 10573–10577 1993b; and Pollard et al., Ann. N.Y. Acad. Sci. 695:165–168, 1993). Moreover, we observed depolarization when external Na$^+$ was replaced by the (usually) impermeant large cations tetraethylammonium+ (TEA$^+$) or N-methyl-D-glucamine$^+$ (NMDG$^+$).

βAβ1-42 was pre-incubated for 48 hrs at pH7.4 and 37° C. before applying the peptide to the neuronal cells. This was because it had been found (Blanchard et al., 1997, Blanchard et al., 2000) that such incubation was necessary to obtain a robust calcium influx. The particular peptide preparation that was used formed mostly fibrils under our aggregation conditions. The literature on the relationship between aggregation of Aβ peptides and neurotoxicity is unclear. In their early experiments, Yankner et al. (*Science* 250:279–282, 1990) did preincubate and observed cell death. Hartley et al. (1999) observed that their protofibrils, "metastable intermediates in amyloid fibril formation", can alter the electrical activity of neurons and are toxic, as was a "low molecular weight Abeta". Walsh et al. (*J. Biol. Chem.* 274:25945–52, 1999) report that their "protofibrils . . . affect the normal metabolism of cultured neurons [sic]". We also saw protofibrils in our EM experiments when the Aβ1-42 sample had not been incubated at 37° C. (Blanchard et al., 2000), but this preparation did not produce the characteristic calcium influx and was therefore deemed to be non-toxic to our cells.

In summary, it appears that aggregated Aβ1-42 acts on the type of AMPA/kainate receptors (and also NMDA receptors) present in hNT neurons that allow Ca$^{2+}$ to flow into the cell. Aggregated Aβ1-42 also acts as an ionophore admitting cations to cause membrane depolarization in neurons. Based on the results shown herein for non-Na ion influx, the ionophore structure formed by aggregated Aβ1-42 would have to be large enough to admit cations as large as TEA$^+$ and NMDG$^+$ (FIG. 16A,B), which may be the case for the so-called giant ionophores previously reported (Arispe et al., 1993a, 1993b, and Pollard et al., 1993). Several models of Aβ1-40 ionophores with the expected properties have been proposed by Durell et al. (*Biophys. J.* 67:2137–2145, 1994), but these models were proposed for Aβ1-40, not Aβ1-42. In particular, one of their models has the C-terminal portion of Aβ1-40 form α-helices which then as a group would insert into the membrane and might form an ion channel; Aβ1-42 has a similar C-terminal sequence. Their model is appealing, but does not explain the basis for the rapid interchange between "large" and "giant" ionophores.

We interpret the observed increase in DiBAC$_4$(3) fluorescence by Aβ1 -42 in our hNT cells as a membrane depolarization. We have also observed similar depolarization effects with PC12 cells (unpublished observations). The magnitude of the depolarization caused by Aβ1-42 (Table 1) can be calculated from a comparison with observations when the membrane was depolarized by partially replacing Na$^+$ with K$^+$ in the bath solution and using the Nernst equilibrium. When the major external cation was Na$^+$, the observed depolarization is in the range of +13.5 to +22.6 mV. Since this is postulated to be a long-lasting, perhaps chronic state and not readily reversible, the affected neurons would be hyperexcitable and respond to certain weak stimuli that are usually ineffective. Thus we postulate this effect as a model for cognitive deficits in Alzheimer brains.

Hartley et al. (1999) recently reported acute electrophysiological changes and neurotoxicity in cultures of embryonic rat brain cells, when exposed to intermediates of Aβ1-40 aggregation. Their so-called "protofibrils", which are fibrils of intermediate length, did not cause cell death, as did fully formed fibrils. However, in patch-clamp experiments the authors were able to demonstrate that protofibrils at micromolar concentration produced a "rapid and sustained increase in electrical activity", including "increased frequencies and larger sizes of membrane depolarizations". The experiments disclosed herein were done under very different conditions, with different cells and with aggregated Aβ1-42, and permit an understanding of the molecular mechanisms involved.

The cell-type-specific distribution of neuronal damage and dysfunction determines the kind of cognitive and behavioral deficits seen in Alzheimer's Disease. It is expected that the events observed in culture reflect the in vivo situation of AD, providing a rational basis for the regional distribution of cell damage observed in AD, namely, the distribution of particular receptors. Given the drastic cellular calcium overload induced by aggregated Aβ1-42, it can be seen that cell-type specific localization of calcium overload, followed by plaques and tangles and neuronal dysfunction is likely related to the distribution of neurons with AMPA/kainate receptors of the kind that transmit Ca$^{2+}$ and with NMDA receptors. Furthermore, it is expected that increased calcium will lead to protein kinase activation, hyperphosphorylated tau and tangle formation.

Therefore, although we do not wish to be limited to any particularl theory, two molecular causes are proposed for neuronal dysfunction in Alzheimer's Disease. First, pre-aggregated Aβ1-42 causes calcium influx by acting through AMPA/kainate receptors and NMDA receptors, leading to a chronic and toxic increase in cytosolic calcium levels in certain neurons. Second, aggregated Aβ1-42 causes the formation of large ionophores that admit cations and produce chronic depolarization. Both effects lead to neuronal dysfunction: the first to disturbance of calcium homeostasis and eventual cell death, the second to hyperexcitability and likely cognitive dysfunction.

REFERENCES

1. Sanderson et al., (1997) *Brain Res.* 744,7–14.
2. Blanchard et al., (1997) *Brain Res.* 776,40–50.
3. Blanchard, B. J., Hiniker, A. E., Lu, C. C., Margolin, Y. & Ingram, V. M., (2000) *J. Alzheimer Disease* (in press).
4. Hartley, D. M., Walsh, D. M., Ye, C. P., Diehl, T., Vasquez, S., Vassilev, P. M., Teplow, D. P. & Selkoe, D. J. (1999) *J. Neuroscience* 19,8876–8884.
5. Hartinger, J., & Jahn, R. (1993) *J. Biol. Chem.* 268, 23122–23127.
6. Cooper, C. E., Bruce, D., & Nicholls, P. (1990) *Biochemistry.* 29, 3859–3865.
7. Langheinrich, U. & Daut, J. (1997) *J Physiol.* 502, 397–408.
8. Bräuner, T., Hülser, D. F., & Strassr, R. J. (1984) *Biochimica et Biophysica Acta* 771, 2208–216.
9. Arispe, N., Rojas, E., & Pollard, H. B. (1993)) *Proc. Natl. Acad. Sci. USA* 90, 567–571.
10. Arispe, N., Pollard, H. B., & Rojas, E. (1993) *Proc. Natl. Acad. Sci. USA* 90, 10573–10577.
11. Pollard, H. B., Rojas, E., & Arispe, N. (1993) *Ann. N.Y. Acad. Sci.* 695,165–168.
12. Kawahara, M., Arispe, N., Kuroda, Y., & Rojas, E. (1997) *Biophys. J.* 73, 67–75.
13. Yankner, B. A., Duffy, L. K. & Kirschner, D. A. (1990). *Science.* 250, 279–282.
14. Walsh, D. M., Hartley, D. M., Kusumoto, Y., Fezoui, Y., Condron, M. M., Lomakin, A., Benedek, G. B., Selkoe, D. J. & Teplow, D. B. (1999) *J Biol. Chem.* 274, 25945–52.
15. Durell, S. R., Guy, H. R., Arispe, N., Rojas, E., & Pollard H. B. (1994) *Biophys. J.* 67, 2137–2145.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

A sequence listing is presented below and is followed by what is claimed.

What is claimed is:

1. A method for identifying lead compounds for a pharmacological agent useful in the treatment of conditions associated with increased neuronal depolarization induced by the presence of β-amyloid peptide (Aβ) aggregates, comprising
   providing a neuronal cell in a medium containing a potentiometric compound, wherein the influx into the neuronal cell of the potentiometric compound upon depolarization of the neuronal cell is detectable,
   forming a mixture comprising a Aβ containing a β-sheet forming domain, and a candidate pharmacological agent,
   incubating the mixture under conditions which, in the absence of the candidate pharmacological agent, permit the Aβ to aggregate,
   contacting the neuronal cell with the mixture, under conditions which, in the presence of Aβ aggregates, permit influx of a control amount of the potentiometric compound into the neuronal cell, and
   detecting the potentiometric compound as a measure of the relative depolarization of the neuronal cell, wherein detection of a lesser amount of potentiometric compound in the neuronal cell than is present when the neuronal cell is contacted with Aβ aggregates indicates that the candidate pharmacological agent is a lead compound for a pharmacological agent which disrupts Aβ aggregation.

2. The method of claim 1 wherein the candidate pharmacological agent is a peptide.

3. The method of claim 1 wherein the candidate pharmacological agent is a small organic molecule having a molecular weight of more than 50 yet less than about 2500.

4. The method of claim 1, wherein the potentiometric compound is fluorescent.

5. The method of claim 4, wherein the potentiometric compound is bis-(1,3-dibutylbarbituric acid)trimethine oxonol (DiBAC$_4$(3)).

6. A method for identifying lead compounds for a pharmacological agent useful in the treatment of conditions associated with increased neuronal depolarization induced by the presence of β-amyloid peptide (Aβ aggregates, comprising
   providing a neuronal cell in a medium containing a potentiometric compound, wherein the influx into the neuronal cell of the potentiometric compound upon depolarization of the neuronal cell is detectable,
   contacting the neuronal cell with Aβ aggregates under conditions which permit influx of a control amount of the potentiometric compound into the neuronal cell,
   detecting the potentiometric compound in the neuronal cell as a measure of depolarization induced by Aβ aggregates,
   contacting the neuronal cell with a candidate pharmacological agent, and
   detecting the potentiometric compound in the neuronal cell as a measure of the relative depolarization of the neuronal cell in the presence of the candidate pharmacological agent, wherein detection of a lesser amount of potentiometric compound in the neuronal cell than is present when the neuronal cell is contacted with Aβ aggregates but not the candidate pharmacological agent indicates that the candidate pharmacological agent is a lead compound for a pharmacological agent which reduces Aβ aggregate induced neuronal cell depolarization.

7. The method of claim 6 wherein the candidate pharmacological agent is a peptide.

8. The method of claim 6 wherein the candidate pharmacological agent is a small organic molecule having a molecular weight of more than 50 yet less than about 2500.

9. The method of claim 6, wherein the potentiometric compound is fluorescent.

10. The method of claim 9, wherein the potentiometric compound is bis-(1,3-dibutylbarbituric acid)trimethine oxonol (DiBAC$_4$(3)).

* * * * *

SEQUENCE LISTING

```
<160> NUMBER OF SEQ ID NOS: 30

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Ile Ala Ala Gly Ile Thr Gly Gly Gly
 1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Thr Val Ile Gly Thr Ile Gly Gly Gly
 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Thr Gly Ile Ile Ala Ser Gly Gly Gly
 1               5

<210> SEQ ID NO 4
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Val Val Ile Ser Gly Ala Gly Gly Gly
 1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Thr Thr Ile Val Ser Thr Gly Gly Gly
 1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Ala Gly Val Ile Ser Ile Gly Gly Gly
 1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Ile Gly Ala Ser Ile Val Gly Gly Gly
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Ser Ile Ala Thr Ser Thr Gly Gly Gly
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Thr Val Ile Arg Thr Ile Ala Ala Ala
 1               5

<210> SEQ ID NO 10
<211> LENGTH: 11
```

```
<212> TYPE: PRT
<213> ORGANISM: Artificial Sequence
<220> FEATURE:
<223> OTHER INFORMATION: Synthetic Peptide

<400> SEQUENCE: 10

Gly Ser Asn Lys Gly Ala Ile Ile Gly Leu Met
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 11

Gly Gly Gly Gly Ser Asn Lys Gly Ala Ile Ile Gly Leu Met
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

Val Val Ile Ser Ala Ala Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Ile Ala Ala Ser Ile Val Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Ser Ile Ala Thr Ser Thr Ala
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15

Thr Val Ile Arg Thr Ile
1               5

<210> SEQ ID NO 16
<211> LENGTH: 5
<212> TYPE: PRT
```

```
<213> ORGANISM: Artificial Sequence
<220> FEATURE:
<223> OTHER INFORMATION: Synthetic Peptide

<400> SEQUENCE: 16

Thr Val Ile Arg Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Thr Pro Ile Arg Thr Pro Ala Pro Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Pro Val Pro Arg Pro Ile Pro Ala Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Thr Pro Ile Arg Thr Pro Ala
1               5

<210> SEQ ID NO 20
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 20

Asp Ala Glu Phe Arg His Asp Ser Gly Tyr Glu Val His His Gln Lys Leu
1               5                   10                  15

Val Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Ser Pro Ala Leu Ala
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 22

Ser Thr Ile Thr Ala
 1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 23

Ser Ser Ser Thr Ala
 1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 24

Ser Ala Pro Ala Ala
 1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Leu Pro Val Leu Ala
 1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Leu Pro Val Ser Ala
 1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Leu Pro Thr Ser Ala
 1               5
```

-continued

```
<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 28

Ser Ser Thr Val Pro Ala
 1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 29

Ser Ser Ala Pro Pro Ala
 1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Ser Ser Thr Val Thr Ala
 1               5
```